US011969233B2

(12) United States Patent
Morris et al.

(10) Patent No.: US 11,969,233 B2
(45) Date of Patent: Apr. 30, 2024

(54) MEASURING CARDIOVASCULAR PRESSURE BASED ON PATIENT STATE

(71) Applicant: Medtronic, Inc., Minneapolis, MN (US)

(72) Inventors: Mary M. Morris, Shoreview, MN (US); Ruth N. Klepfer, St. Louis Park, MN (US); Karen J. Kleckner, Blaine, MN (US); Joel R. Lauer, Clearwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 797 days.

(21) Appl. No.: 16/885,396

(22) Filed: May 28, 2020

(65) Prior Publication Data

US 2020/0288989 A1 Sep. 17, 2020

Related U.S. Application Data

(63) Continuation of application No. 15/384,547, filed on Dec. 20, 2016, now abandoned.

(51) Int. Cl.
*A61B 5/0215* (2006.01)
*A61B 5/00* (2006.01)
(Continued)

(52) U.S. Cl.
CPC .......... *A61B 5/0215* (2013.01); *A61B 5/0024* (2013.01); *A61B 5/0031* (2013.01);
(Continued)

(58) Field of Classification Search
None
See application file for complete search history.

(56) References Cited

U.S. PATENT DOCUMENTS 5,117,824 A 6/1992 Keimel et al.
5,545,186 A 8/1996 Olson et al.
(Continued)

FOREIGN PATENT DOCUMENTS

WO WO-0240096 A1 * 5/2002 ......... A61N 1/36521
WO 2012151302 A1 11/2012

OTHER PUBLICATIONS

Laulive, JL. "Pulmonary Artery Pressures and Position Changes in the Critically Ill Adult." Dimens Crit Care Nurs. Jan.-Feb. 1982;1(1):28-34. (Year: 1982).*

(Continued)

*Primary Examiner* — Meredith Weare
(74) *Attorney, Agent, or Firm* — Shumaker & Sieffert, P.A.

(57) ABSTRACT

A method for monitoring a cardiovascular pressure in a patient includes measuring, by pressure sensing circuitry of an implantable pressure sensing device, the cardiovascular pressure of the patient. The method further includes transmitting, via wireless communication circuitry of the implantable pressure sensing device, the measured cardiovascular pressure to another device. The method further includes determining, by processing circuitry of the other device, whether a posture of the patient at a time of the measured cardiovascular pressure was a target posture for cardiovascular pressure measurements. The method further includes determining, by the processing circuitry of the other device, whether to store or discard the transmitted cardiovascular pressure based on determining whether the posture was the target posture.

21 Claims, 16 Drawing Sheets

(51) Int. Cl.
- *A61B 5/0245* (2006.01)
- *A61B 5/07* (2006.01)
- *A61B 5/08* (2006.01)
- *A61B 5/11* (2006.01)
- *A61N 1/365* (2006.01)

(52) U.S. Cl.
CPC .......... *A61B 5/4561* (2013.01); *A61B 5/4836* (2013.01); *A61B 5/6876* (2013.01); *A61B 5/6882* (2013.01); *A61B 5/7221* (2013.01); *A61B 5/7285* (2013.01); *A61B 5/002* (2013.01); *A61B 5/0022* (2013.01); *A61B 5/0245* (2013.01); *A61B 5/076* (2013.01); *A61B 5/0816* (2013.01); *A61B 5/1116* (2013.01); *A61B 5/1118* (2013.01); *A61B 5/6883* (2013.01); *A61B 5/746* (2013.01); *A61B 2562/0219* (2013.01); *A61B 2562/0247* (2013.01); *A61B 2562/162* (2013.01); *A61N 1/36564* (2013.01)

(56) References Cited

U.S. PATENT DOCUMENTS

| | | | |
|---|---|---|---|
| 5,755,736 | A | 5/1998 | Gillberg et al. |
| 6,438,408 | B1 | 8/2002 | Mulligan et al. |
| 6,738,667 | B2 | 5/2004 | Deno et al. |
| 7,488,290 | B1 | 2/2009 | Stahmann et al. |
| 8,864,676 | B2 | 10/2014 | Beasley et al. |
| 2005/0027323 | A1 | 2/2005 | Mulligan et al. |
| 2005/0061319 | A1* | 3/2005 | Hartley ............... A61B 5/4812 128/204.23 |
| 2006/0041281 | A1* | 2/2006 | Von Arx ............ A61B 5/02108 607/18 |
| 2006/0116593 | A1 | 6/2006 | Zhang et al. |
| 2006/0224190 | A1 | 10/2006 | Gill et al. |
| 2007/0088220 | A1 | 4/2007 | Stahmann |
| 2007/0088221 | A1 | 4/2007 | Stahmann |
| 2007/0142868 | A1 | 6/2007 | Moon et al. |
| 2007/0156057 | A1 | 7/2007 | Cho et al. |
| 2007/0161912 | A1 | 7/2007 | Zhang et al. |
| 2008/0171941 | A1* | 7/2008 | Huelskamp ........... A61B 5/0205 600/484 |
| 2008/0177350 | A1 | 7/2008 | Kieval et al. |
| 2008/0195165 | A1* | 8/2008 | Stahmann ............ A61B 5/0215 607/18 |
| 2008/0262361 | A1 | 10/2008 | Gutfinger et al. |
| 2008/0294060 | A1* | 11/2008 | Haro ..................... A61B 5/03 600/538 |
| 2009/0312650 | A1* | 12/2009 | Maile ................. A61B 5/0215 600/486 |
| 2010/0030292 | A1 | 2/2010 | Sarkar et al. |
| 2010/0249864 | A1* | 9/2010 | Jarverud ............ A61B 5/02028 600/595 |
| 2010/0331713 | A1 | 12/2010 | Ostrow |
| 2012/0130991 | A1 | 5/2012 | Atas et al. |
| 2012/0283580 | A1 | 11/2012 | Havel et al. |
| 2013/0298636 | A1 | 11/2013 | Hatlestad et al. |
| 2014/0276928 | A1 | 9/2014 | Vanderpool et al. |
| 2016/0310031 | A1 | 10/2016 | Sarkar |
| 2016/0331884 | A1 | 11/2016 | Sigg et al. |
| 2017/0056669 | A1* | 3/2017 | Kane ................. A61N 1/36521 |
| 2018/0168502 | A1 | 6/2018 | Cho et al. |

OTHER PUBLICATIONS

Aitken, LM. "Comparison of Pulmonary Artery Pressure Measurements in the Supine and 60° Lateral Positions." Aust Crit Care. Dec. 1995;8(4):21, 24-9. (Year: 1995).*

Fujise et al. "The Effects of the Lateral Position on Cardiopulmonary Function During Laparoscopic Urological Surgery." Anesth Analg. Oct. 1998;87(4):925-30. (Year: 1998).*

"Pulmonary Artery." Wikipedia. Retrieved Sep. 21, 2023. https://en.wikipedia.org/wiki/Pulmonary_artery (Year: 2023).*

Communication pursuant to Article 94(3) EPC from counterpart European Application No. 17829455.9 dated May 23, 2022, 6 pp.

Second Office Action and Search Report, and translation thereof, from counterpart Chinese Application No. 201780078822.3 dated Apr. 6, 2022, 17 pp.

First Office Action and Search Report, and translation thereof, from counterpart Chinese Application No. 201780078822.3 dated Sep. 23, 2021, 11 pp.

Response to Examination Report dated May 23, 2022, from counterpart European Application No. 17829455.9 filed Sep. 13, 2022, 5 pp.

(PCT/US2017/067196) PCT Notification of Transmittal of the International Search Report and the Written Opinion of the International Searching Authority, dated Feb. 12, 2018, 12 pages.

U.S. Appl. No. 62/370,113, by Bruce D. Gunderson, filed Aug. 2, 2016. 69 pgs.

* cited by examiner

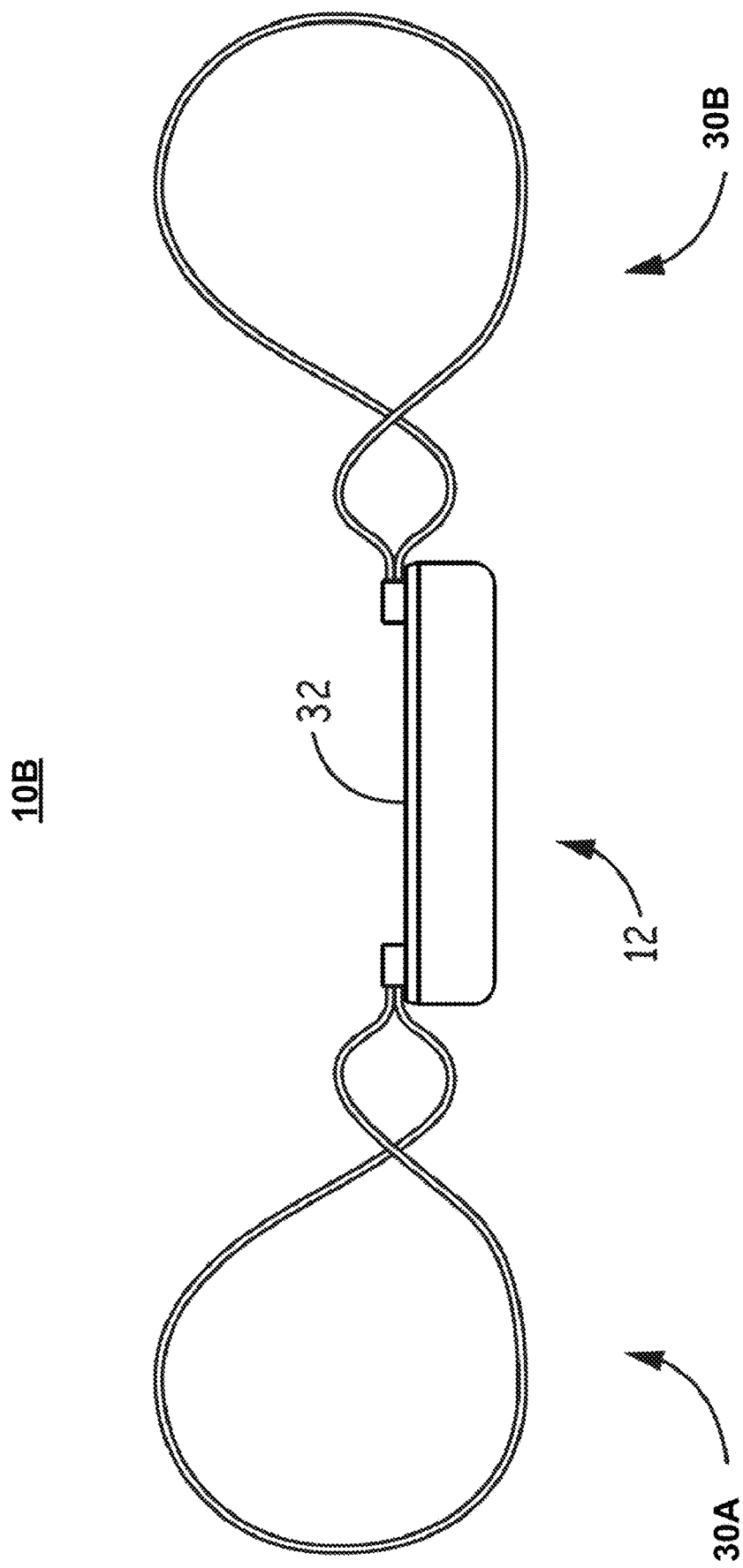

MEASURING CARDIOVASCULAR PRESSURE BASED ON PATIENT STATE

TECHNICAL FIELD

The disclosure relates to medical device systems, more particularly, measurement of cardiovascular pressure by medical device systems.

BACKGROUND

Various implantable medical devices have been clinically implanted or proposed for therapeutically treating or monitoring one or more physiological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, and pressure sensors, among others. Such devices may be associated with leads to position electrodes or sensors at a desired location, or may be leadless, with the ability to wirelessly transmit data either to another device implanted in the patient or to another device located externally of the patient, or both.

By way of illustrative example, implantable miniature sensors have been proposed and used in blood vessels to measure directly the diastolic, systolic and mean blood pressures, as well as body temperature and cardiac output. As one example, patients with chronic cardiovascular conditions, particularly patients suffering from chronic heart failure, may benefit from the use of implantable sensors adapted to monitor blood pressures. As another example, subcutaneously implantable monitors have been proposed and used to monitor heart rate and rhythm, as well as other physiological parameters, such as patient posture and activity level. Such direct in vivo measurement of physiological parameters may provide significant information to clinicians to facilitate diagnostic and therapeutic decisions. If linked electronically to another implanted therapeutic device (e.g., a pacemaker), the data can be used to facilitate control of that device. Such devices also, or alternatively, may be wirelessly linked to an external receiver.

SUMMARY

In general, this disclosure is directed to techniques for measuring cardiovascular pressure. The example techniques may include measuring cardiovascular pressure of a patient within a predetermined window of time during the day. A medical device may also determine the state, e.g., posture, activity level, and/or heart rate, of the patient at the time of each cardiovascular pressure measurement. The measurement of cardiovascular pressure may be stored or discarded based on whether the state of the patient at the time of the cardiovascular pressure measurement was a target state, e.g., target posture. In some examples, the cardiovascular pressure measurements taken when the patient is in the target state may be used to evaluate the condition of the patient.

As one example, the disclosure is directed to a method for monitoring a cardiovascular pressure in a patient, the method including measuring, by pressure sensing circuitry of an implantable pressure sensing device, the cardiovascular pressure of the patient. The method further includes transmitting, via wireless communication circuitry of the implantable pressure sensing device, the measured cardiovascular pressure to another device. The method further includes determining, by processing circuitry of the other device, whether a posture of the patient at a time of the measured cardiovascular pressure was a target posture for cardiovascular pressure measurements. The method further includes determining, by the processing circuitry of the other device, whether to store or discard the transmitted cardiovascular pressure based on determining whether the posture was the target posture.

A medical device system for monitoring a cardiovascular pressure in a patient, the medical device system including an implantable pressure sensing device including wireless communication circuitry and pressure sensing circuitry configured to measure the cardiovascular pressure of the patient. The implantable pressure sensing device further includes processing circuitry configured to control the pressure sensing circuitry to measure the cardiovascular pressure of the patient. The processing circuitry of the implantable pressure sensing device is further configured to transmit the measured cardiovascular pressure to another device via the wireless communication circuitry. The medical device system further includes the other device including processing circuitry configured to determine whether a posture of a patient at the time of the measured cardiovascular pressure was a target posture for cardiovascular pressure measurements. The processing circuitry of the other device is further configured to determine whether to store or discard the transmitted cardiovascular pressure based on determining whether the posture was the target posture.

As another example, the disclosure is directed to a method for monitoring a cardiovascular pressure in a patient, the method including determining, by processing circuitry of an implantable monitoring device, that a time of day is within a predetermined window for cardiovascular pressure measurements. The method further includes sensing, with sensing circuitry of the implantable monitoring device, posture of the patient during the predetermined window in response to the determination. The method further includes determining, by the processing circuitry of the implantable monitoring device, that the sensed posture of the patient is a target posture for cardiovascular pressure measurements. The method further includes sending a trigger signal, via wireless communication circuitry of the implantable monitoring device, to an implantable pressure sensing device, wherein the implantable pressure sensing device measures the cardiovascular pressure of the patient using pressure sensing circuitry in response to the trigger signal. The method further includes receiving, by the processing circuitry of the implantable monitoring device, the measured cardiovascular pressure of the patient from the implantable pressure sensing device via the wireless communication circuitry of the implantable monitoring device.

As another example, the disclosure is directed to a medical device system for monitoring a cardiovascular pressure in a patient, where the medical device system comprises an implantable monitoring device comprising wireless communication circuitry, processing circuitry configured to determine that a time of day is within a predetermined window for cardiovascular pressure measurements, and sensing circuitry configured to sense a posture of the patient during the predetermined window in response to the determination. The processing circuitry is further configured to determine that the sensed posture of the patient is a target posture for cardiovascular pressure measurements. The wireless communication circuitry is configured to send a trigger signal to an implantable pressure sensing device. The medical device system further comprises the implantable pressure sensing device comprising wireless communication circuitry configured to receive the trigger signal and pressure sensing circuitry configured to measure the cardiovascular pressure of the patient in response to the trigger signal. The wireless communication circuitry of the implantable pressure sensing device is further configured to transmit the measured cardiovascular pressure of the patient to the implantable monitoring device.

As another example, the disclosure is directed to a method for monitoring a cardiovascular pressure in a patient, the method comprising determining, by processing circuitry of an implantable pressure sensing device, that a time of day is within a predetermined window for cardiovascular pressure measurements. The method further includes measuring, by pressure sensing circuitry of the implantable pressure sensing device, the cardiovascular pressure of the patient in response to the determination. The method also includes transmitting, via wireless communication circuitry of the implantable pressure sensing device, the measured cardiovascular pressure to another device. The method includes determining, by processing circuitry of the other device, whether a posture of the patient at the time of day was a target posture for cardiovascular pressure measurements, wherein the target posture comprises a supine posture, a right-side-down posture when the implantable pressure sensing device is implanted in the left pulmonary artery, or a left-side-down posture when the implantable pressure sensing device is implanted in the right pulmonary artery. The method further includes determining, by the processing circuitry of the other device, whether to store or discard the transmitted cardiovascular pressure based on determining whether the posture was the target posture.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

FIG. 2B illustrates a side profile view of another example sensor assembly.

The drawings and the description provided herein illustrate and describe various examples of the inventive methods, devices, and systems of the present disclosure. However, the methods, devices, and systems of the present disclosure are not limited to the specific examples as illustrated and described herein, and other examples and variations of the methods, devices, and systems of the present disclosure, as would be understood by one of ordinary skill in the art, are contemplated as being within the scope of the present application.

DETAILED DESCRIPTION

Cardiovascular pressure, such as pulmonary artery pressure (PAP), may be significantly affected by body position or orientation during the pressure measurement. Consequently, PAP is traditionally clinically measured with the patient at rest, awake, and supine (i.e., lying on their back). An implantable pressure sensing device may unobtrusively take measurements under similar conditions by being configured to measure PAP (or other cardiovascular pressure measurements) at night, e.g., between midnight and 4 am, when the patient is more likely to be at rest and supine.

However, a patient may not necessarily be asleep at night when the automatic pressure measurements are scheduled and, if asleep, may not be in the supine posture. Posture (e.g., body position or orientation) may significantly affect the cardiovascular pressure value measured by an implantable pressure sensing device due to changes in cardiac output and the hydrostatic blood column above sensing device. For example, in an experiment using a porcine model, the pressure in the left pulmonary artery increased by 12 mmHg when the position was changed from dorsal down recumbency to left lateral recumbency.

This disclosure describes example techniques related to measuring cardiovascular pressure within a predetermined window of time during the day. The measurements may be matched with concurrent measurements of patient state, e.g., posture, activity level, and/or heart rate, where the cardiovascular pressure measurements are discarded or stored based on the patient state measurements. As a result, the stored cardiovascular pressure measurements may form a dataset with similar patient state, allowing a practitioner to better evaluate the condition of the patient, e.g., whether the condition of the patient changed from over time. In the following description, references are made to illustrative examples. It is understood that other examples may be utilized without departing from the scope of the disclosure.

Figure 1A:
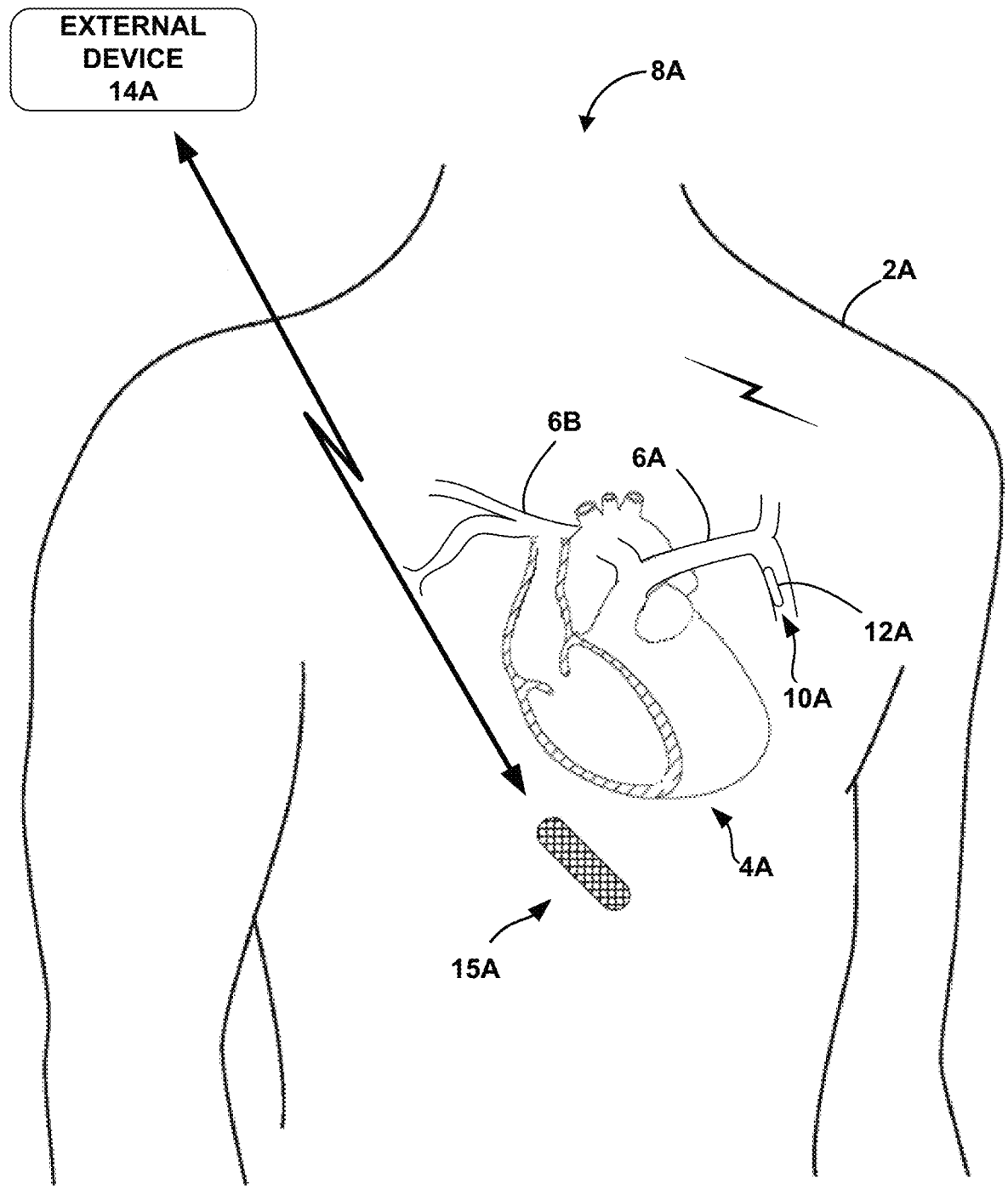
FIG. 1A is a conceptual drawing illustrating an example medical device system in conjunction with a patient.

FIG. 1A is a conceptual drawing illustrating an example medical device system 8A in conjunction with a patient 2A. Medical device system 8A is an example of a medical device system configured to implement the techniques described herein for monitoring cardiovascular pressure and other physiological parameters of patient 2A, such as blood pressure and body position or posture, patient motion or activity, and/or heart rate, and determining whether to store or discard a measurement of cardiovascular pressure based on the state of patient 2A at the time of the cardiovascular pressure measurement. In the illustrated example, medical device system 8A includes an implantable medical device (IMD) 15A, also referred to as implantable monitoring device 15A or an implantable hub device, in communication with external device 14A. Medical device system 8A also includes implantable pressure sensing device 12A, also referred to as sensor device 12A or sensor device 12A. For purposes of this description, knowledge of cardiovascular anatomy is presumed and details are omitted except to the extent necessary or desirable to explain the context of the techniques of this disclosure.

As shown in FIG. 1A, implantable sensor assembly 10A may be implanted within pulmonary artery 6A of heart 4A. In some examples, pulmonary artery 6A of heart 4A may comprise a left pulmonary artery, and pulmonary artery 6B may comprise a right pulmonary artery. Although FIG. 1A depicts sensing device 12A positioned in a descending branch of the left pulmonary artery, sensing device 12A may positioned elsewhere with the left pulmonary artery, in the right pulmonary artery, or any suitable region of the patient's cardiovascular system. For the sake of clarity, a fixation assembly for sensor assembly 10A is not depicted in FIG. 1A. A suitable fixation assembly configured to secure sensor assembly 10A within pulmonary artery 6A will be discussed below with respect to FIGS. 2A-4B.

In the illustrated example, IMD 15A is an insertable cardiac monitor (ICM) capable of sensing and recording cardiac electrogram (EGM) signals from a position outside of heart 4A via electrodes, and will be referred to as ICM 15A hereafter. In some examples, ICM 15A includes or is coupled to one or more additional sensors, such as accelerometers, that generate one or more signals that vary based on patient motion and/or posture, blood flow, or respiration. ICM 15A may monitor a physiological parameter indicative of patient state, such as posture, heart rate, activity level, heart rate, and/or respiration rate, and ICM 15A may measure the physiological parameter(s) at times when sensor device 12A is measuring cardiovascular pressure. ICM 15A may include processing circuitry to determine whether the measured posture of patient 2A is a target posture for cardiovascular pressure measurements, wherein the target posture may include a supine posture, i.e., lying on one's back. ICM 15A may be implanted outside of the thorax of patient 2A, e.g., subcutaneously or submuscularly, such as the pectoral location illustrated in FIG. 1A. ICM 15A may be positioned near the sternum near or just below the level of heart 4A. In some examples, ICM 15A may take the form of a Reveal LINQ™ ICM, available from Medtronic plc, of Dublin, Ireland.

Sensor device 12A may be implanted, as one example, within a pulmonary artery of patient 2A and may include pressure sensing circuitry configured to measure the cardiovascular pressure of patient 2A. In some examples, sensor device 12A may be a part of sensor assembly 10A. Each of sensor device 12A and ICM 15A may include a timer and processing circuitry configured to determine a time of day based on the timer value. If sensor device 12A determines that the current time is within a predetermined window that may be stored in memory of sensor device 12A, sensor device 12A may measure and transmit the cardiovascular pressure of patient 2A to ICM 15A. In some examples, sensor device 12A may include wireless communication circuitry configured to receive a trigger signal from ICM 15A. The pressure sensing circuitry of sensor device 12A may be configured to measure the cardiovascular pressure of patient 2A in response to receiving the trigger signal. In this manner, ICM 15A may dictate the times at which sensor device 12A measures cardiovascular pressure, and sensor device 12A may enter a low-power mode such as sleep mode until the wireless communication circuitry of sensor device 12A receives a trigger signal.

ICM 15A may transmit posture data, and other physiological parameter data acquired by ICM 15A, to external device 14A. ICM 15A may also transmit cardiovascular pressure measurements received from sensor device 12A to external device 14A. For example, ICM 15A may transmit any data described herein related to cardiovascular pressure, posture, heart rate, activity level, respiration rate, and/or other physiological parameters to external device 14A. In some examples, the processing circuitry of ICM 15A may first determine whether to store or discard the cardiovascular pressure measurements based on the posture or other state of patient 2A at the time of each cardiovascular pressure measurement. In some examples, processing circuitry of ICM 15A may send all pressure measurements received from sensor device 12A, along with patient state measurements made by ICM 15A, to external device 14A, and the external device or another networked computing device may determine whether to store or discard the cardiovascular pressure measurements based on the posture or other state of patient 2A at the time of each cardiovascular pressure measurement. For purposes of this disclosure, a cardiovascular pressure measurement may include one or more numerical values such as a systolic value and/or a diastolic value, a waveform of the cardiovascular pressure, and/or any other data relating to cardiovascular pressure.

External device 14A may be a computing device, e.g., used in a home, ambulatory, clinic, or hospital setting, to communicate with ICM 15A via wireless telemetry. External device 14A may be coupled to a remote patient monitoring system, such as Carelink®, available from Medtronic plc, of Dublin, Ireland. External device 14A may be, as examples, a programmer, external monitor, or consumer device, e.g., smart phone. In some examples, external device 14A may receive time-stamped data from ICM 15A. The time-stamped data may include measurements of cardiovascular pressure, the posture of patient 2A, and other parameters such as heart rate and respiration rate. The remote patient monitoring system may correlate and assess the time-stamped data as described further herein.

External device 14A may be used to program commands or operating parameters into ICM 15A for controlling its functioning, e.g., when configured as a programmer for ICM 15A. External device 14A may be used to interrogate ICM 15A to retrieve data, including device operational data as well as physiological data accumulated in IMD memory. The interrogation may be automatic, e.g., according to a schedule, or in response to a remote or local user command. Programmers, external monitors, and consumer devices are examples of external devices 14A that may be used to interrogate ICM 15A. Examples of communication techniques used by ICM 15A and external device 14A include radiofrequency (RF) telemetry, which may be an RF link established via Bluetooth, WiFi, or medical implant communication service (MICS).

Medical device system 8A is an example of a medical device system configured to monitor the cardiovascular pressure of patient 2A. The techniques described herein may be performed by processing circuitry of medical device system 8A, such as processing circuitry of one or more of ICM 15A, sensor device 12A, and external device 14A, individually, or collectively. The techniques include determining a time of day and determining whether the time is within a predetermined window for cardiovascular pressure measurements. The pressure sensing circuitry of sensor device 12A may measure the cardiovascular pressure of patient 2A in response to determining that the time is within the predetermined window. The wireless communication circuitry of sensor device 12A may transmit the measured cardiovascular pressure to ICM 15A.

The processing circuitry of ICM 15A may determine whether a posture of patient 2A at the time of the cardiovascular pressure measurement was a target posture for cardiovascular pressure measurements. The processing circuitry of ICM 15A may determine whether to store or discard the transmitted cardiovascular pressure based on determining whether the posture of patient 2A was the target posture at the time of the cardiovascular pressure measurement. In some examples, the processing circuitry of sensor device 12A or ICM 15A may determine the time of day and whether the time is within the predetermined window. If the processing circuitry of ICM 15A determines whether the time is within the predetermined window, ICM 15A may send a triggering signal to sensor device 12A, and sensor device 12A may measure and transmit the cardiovascular pressure to ICM 15A in response to receiving the triggering signal. In some examples, the communication between ICM 15A and sensor device 12A may be radio frequency communication, tissue conductive communication, and/or any other suitable form of communication.

Figure 1B:
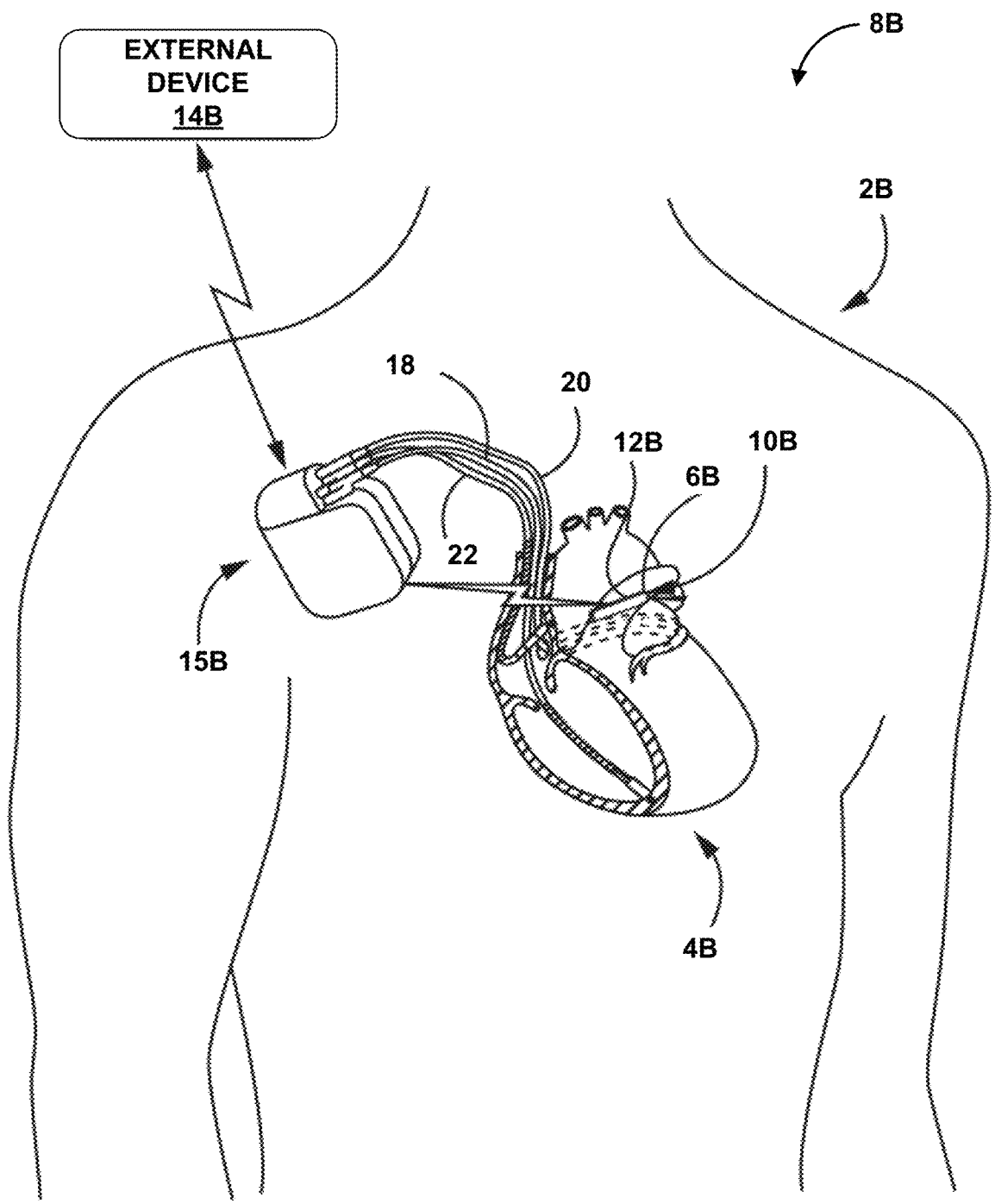
FIG. 1B is a conceptual diagram illustrating another example medical device system in conjunction with a patient.

Another example medical device system that may be configured to implement the techniques is described with respect to FIG. 1B. Although described herein primarily in the context of implantable medical devices monitoring cardiovascular pressure, a medical device system that implements the techniques described in this disclosure may additionally or alternatively include an external medical device, e.g., external cardiac monitor, and/or external pacemaker, cardioverter and/or defibrillator, configured to process measurements of cardiovascular pressure and other parameters.

FIG. 1B is a conceptual diagram illustrating another example medical device system 8B in conjunction with a patient 2B. In the illustrated example, medical device system 8B includes a sensor assembly 10B implanted, for example, in the patient's pulmonary artery 6B through which blood flows from the heart 4B to the lungs, and another IMD 15B. Medical device system 8B is another example of a medical device system configured to implement the techniques described herein for monitoring cardiovascular pressure and other physiological parameters of patient 2B, such as blood pressure and body position or posture, patient motion or activity, and/or heart rate, and determining whether to store or discard a measurement of cardiovascular pressure based on the state of patient 2B at the time of the cardiovascular pressure measurement. The sensor device 12B, IMD 15B, and external device 14B in FIG. 1B may provide substantially similar functionality, e.g., with respect to the techniques described herein for monitoring cardiovascular pressure and other physiological parameters of a patient, as the like numbered device described above with respect to FIG. 1A.

IMD 15B may have one or more leads 18, 20, 22 including electrodes that are placed on or near selected portions of the cardiac anatomy in order to perform the functions of IMD 15B as is well known to those skilled in the art. For example, IMD 15B may be configured to sense and record cardiac EGM signals via the electrodes on leads 18, 20, 22. IMD 15B may also be configured to deliver therapeutic signals, such as pacing pulses, cardioversion shocks, or defibrillation shocks, to heart 4B via the electrodes. In the illustrated example, IMD 15B may be a pacemaker, cardioverter, and or defibrillator.

In some examples, this disclosure may refer to IMD 15B, particularly with respect to its functionality as part of a medical device system that monitors cardiovascular pressure and other physiological parameters of a patient 2, as an implantable monitoring device or implantable hub device. In some examples, IMD 15B includes or is coupled to one or more additional sensors, such as accelerometers, that generate one or more signals that vary based on patient motion and/or posture, blood flow, or respiration. IMD 15B may monitor a physiological parameter indicative of patient state, such as posture, heart rate, activity level, heart rate, and/or respiration rate, and ICM 15B may measure the physiological parameter(s) at times when sensor device 12B is measuring cardiovascular pressure. IMD 15B may include processing circuitry to determine whether the measured posture of patient 2B is a target posture for cardiovascular pressure measurements, wherein the target posture may include a supine posture, i.e., lying on one's back. The target posture may also include lying on one's right side when sensor device 12B is implanted in the left pulmonary artery, referred to as a right supine posture, or lying on one's left side when sensor device 12B is implanted in the right pulmonary artery, referred to as a left supine posture.

IMD 15B also may have wireless capability to receive and transmit, by telemetry, signals relating to operation of the device, and to receive programming commands. IMD 15B may communicate wirelessly to an external device such as external device 14B or to another implanted device such as a sensor device 12B of the sensor assembly 10B. For sake of clarity, sensor assembly 10B is shown without a fixation assembly in FIG. 1B. The sensor device 12B also may communicate wirelessly with external device 14B to provide in vivo data for selected physiological parameters to an external site to inform clinicians of the patient's status. In some examples, sensor device 12B may communicate wirelessly and directly with external device 14B, rather than communicating with external device 14B through IMD 15B. In a similar way, sensor device 12A of FIG. 1A may communicate wirelessly and directly with external device 14A.

Medical device system 8B is an example of a medical device system configured to monitor the cardiovascular pressure of patient 2B. The techniques described herein may be performed by processing circuitry of medical device system 8B, such as processing circuitry of one or more of IMD 15B, sensor device 12B, and external device 14B, individually, or collectively. The techniques include determining a time of day and determining whether the time is within a predetermined window for cardiovascular pressure measurements. The pressure sensing circuitry of sensor device 12B may measure the cardiovascular pressure of patient 2B in response to determining that the time is within the predetermined window. The wireless communication circuitry of sensor device 12B may transmit the measured cardiovascular pressure to IMD 15B.

The processing circuitry of IMD 15B may determine whether a posture of patient 2B at the time of the cardiovascular pressure measurement was a target posture for cardiovascular pressure measurements. The processing circuitry of IMD 15B may determine whether to store or discard the transmitted cardiovascular pressure based on determining whether the posture of patient 2B was the target posture at the time of the cardiovascular pressure measurement. In some examples, the processing circuitry of sensor device 12B or IMD 15B may determine the time of day and whether the time is within the predetermined window. If the processing circuitry of IMD 15B determines whether the time is within the predetermined window, IMD 15B may send a triggering signal to sensor device 12B, and sensor device 12B may measure and transmit the cardiovascular pressure to IMD 15B in response to receiving the triggering signal.

Figure 2A:
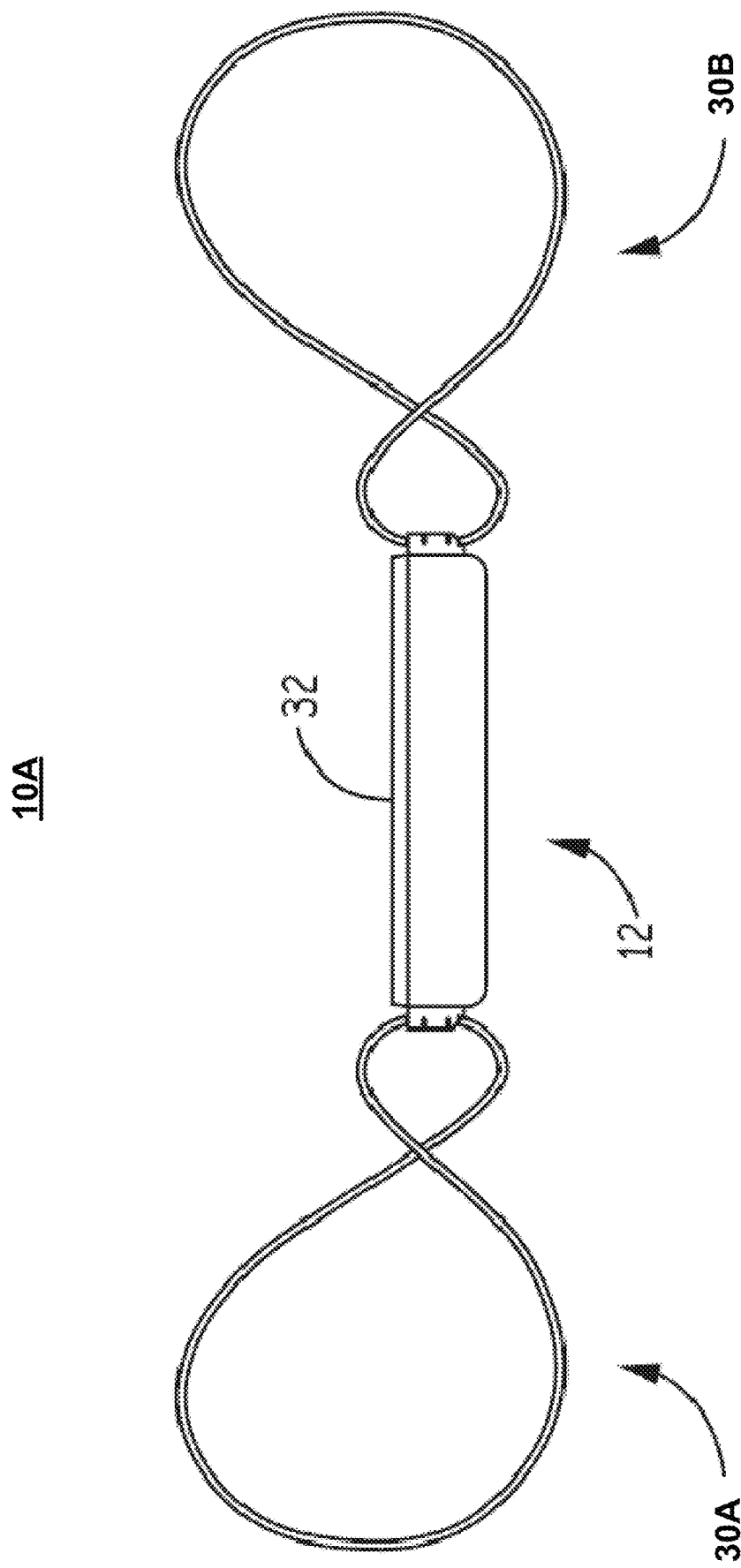
FIG. 2A illustrates a side profile view of an example sensor assembly.

FIGS. 2A-4B illustrate examples of sensor assemblies adapted for minimally invasive placement in a patient's blood vessel, the assembly being shown in its expanded, deployment configuration. Turning first to FIGS. 2A-2B, side profile views of example configurations of sensor assembly 10A and sensor assembly 10B (individually "sensor assembly 10" or collectively "sensor assemblies 10") are depicted. Each of sensor assemblies 10 includes a sensor 12 coupled to fixation members 30A, 30B (collectively "fixation assembly 30"). The fixation assembly 30 and sensor 12 are arranged to enable the sensor assembly 10 to be provided in a delivery configuration that enables it to be navigated to an implant location where it can be deployed into the deployment configuration. As described in this disclosure, it should be understood that the delivery configuration defines a pitch, width or diameter that is narrower, in relation to the deployment configuration, along a common plane. Upon release, the fixation assembly expands into the deployment configuration so as to be in physical contact with the wall of the blood vessel to maintain the positional integrity of sensor device 12. In one example, the fixation assembly will engage the interior wall of the vessel defining the blood flow lumen. The sensor device 12 is attached to the fixation assembly 30 in a manner such that the sensing element 32 of the sensor device 12 is spaced from the wall of the vascular lumen to minimize adverse obstruction to blood flow through the lumen and to position the sensing element 32 of the sensor device 12 to be fully exposed to the blood in the vessel, without obstruction from the housing of the sensor or the vessel wall.

Figure 3A:
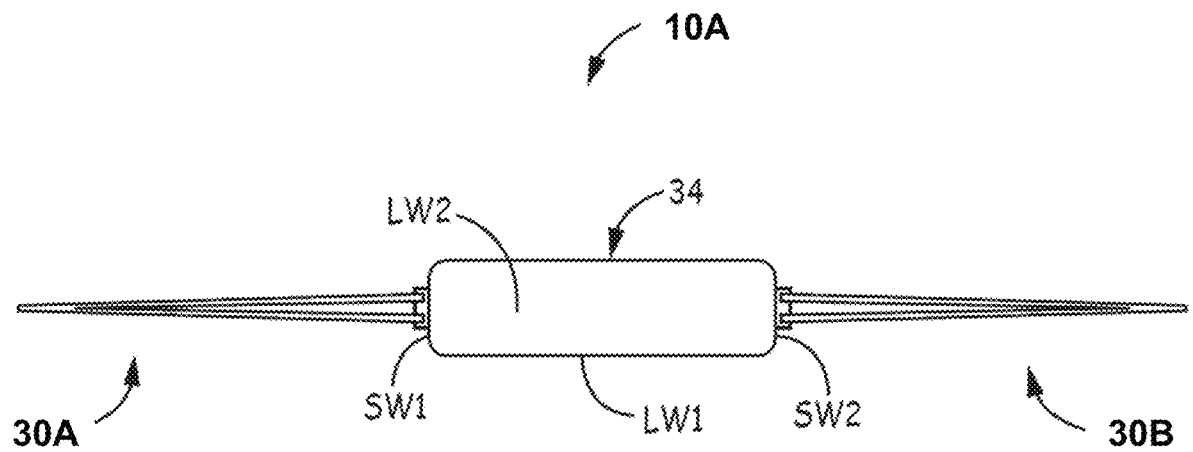
FIG. 3A illustrates a bottom perspective view of the example sensor assembly of FIG. 2A.
Figure 3B:
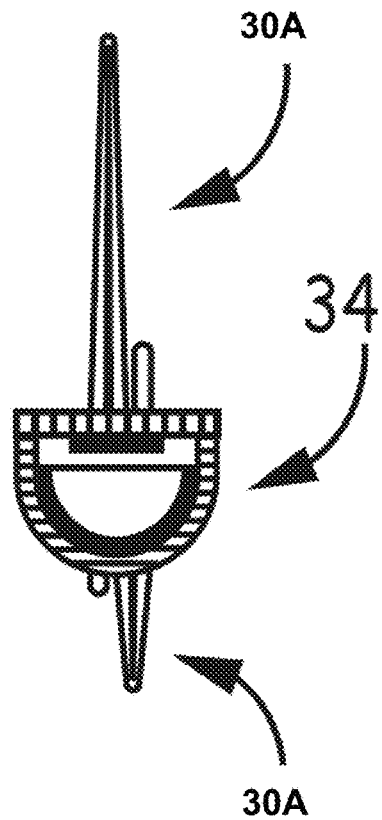
FIG. 3B illustrates a side cross-sectional view of the example sensor assembly of FIG. 2A.

FIG. 3A illustrates a bottom perspective view of the sensor assembly 10A and FIG. 3B illustrates a side cross-sectional view of the sensor assembly 10A. The sensor device 12 includes a capsule 34 that forms a hermetically sealed housing that encloses the operational components such as the electronic circuitry of the sensor assembly 10A. The capsule 34 defines longitudinal walls e.g., LW1, LW2, that extend from a first lateral side wall SW1 to a second lateral sidewall SW2. The longitudinal walls define the longitudinal axis of the sensor device 12. As will be described in more detail with reference to FIG. 4, the fixation members 30A, 30B are coupled to an exterior of the capsule 34 such as the first and second sidewalls, respectively.

Figure 4A:
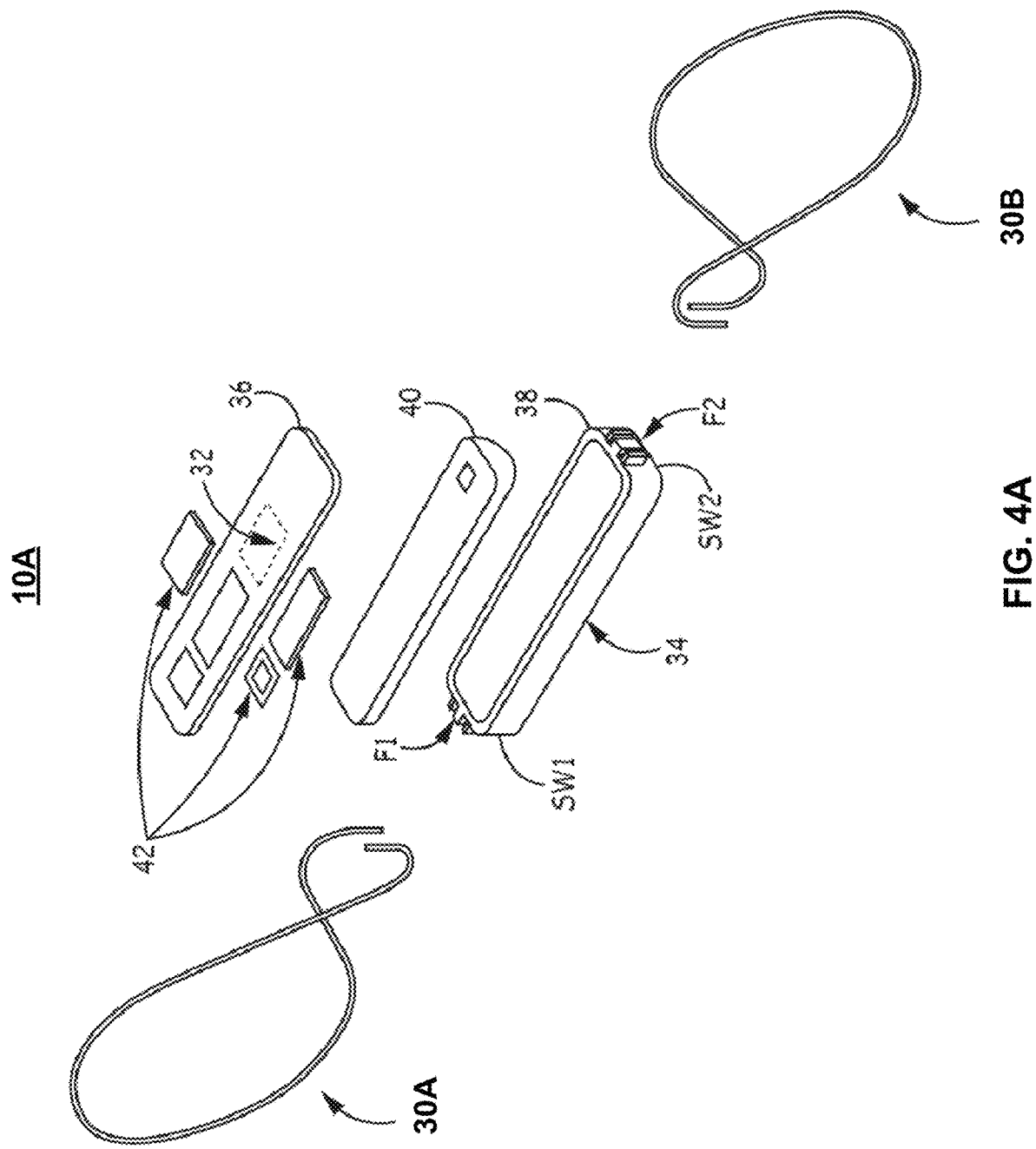
FIG. 4A is an exploded perspective view of example configurations of an example sensor assembly.
Figure 4B:
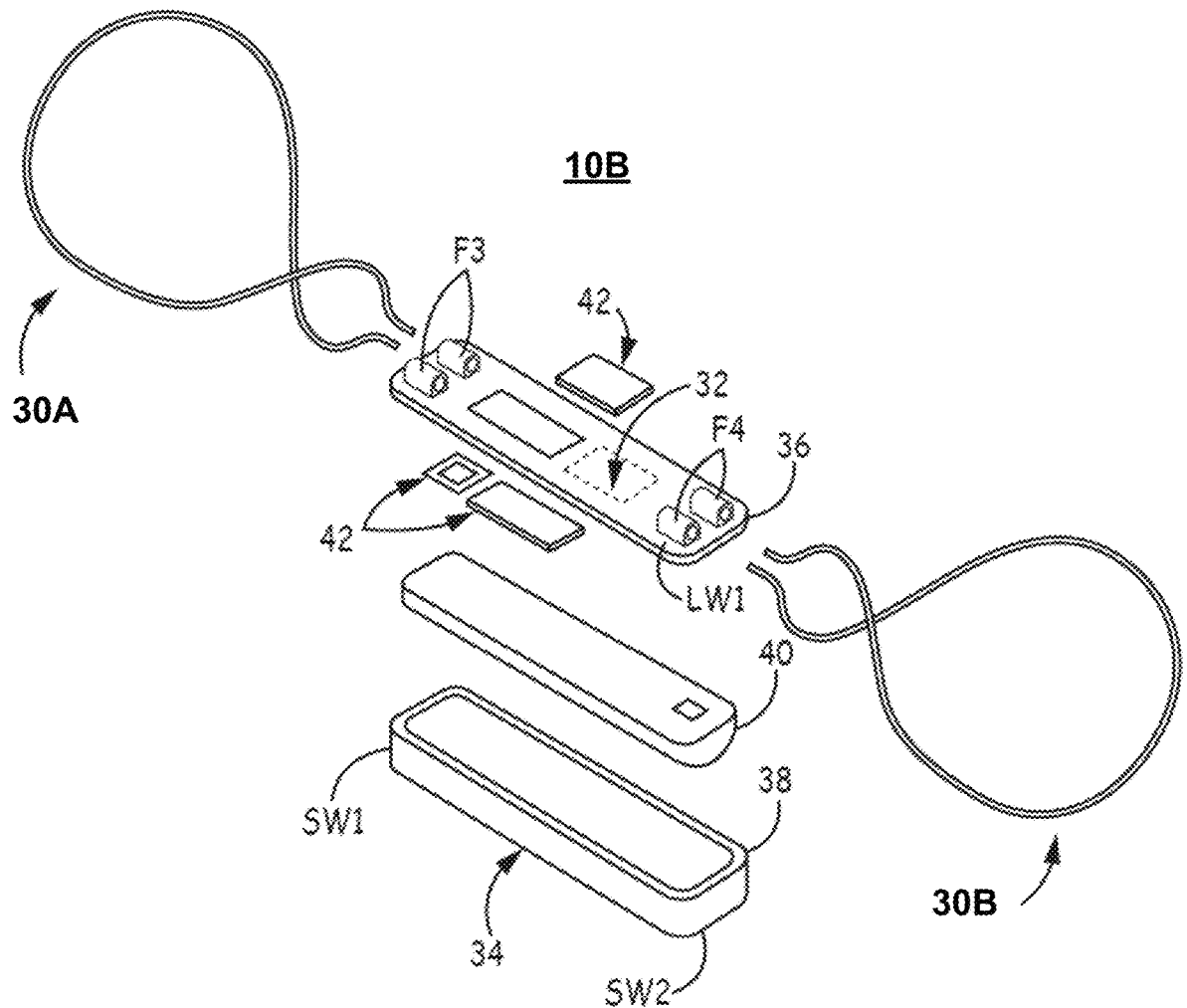
FIG. 4B is an exploded perspective view of example configurations of an example sensor assembly.

FIGS. 4A and 4B are exploded perspective views of example configurations of the example sensor assemblies 10A and 10B, respectively. The capsule 34 of the sensor device 12 may include an elongate body that defines an interior cavity. The interior cavity of the capsule 34 is sized and shaped to contain the battery 40, and electronics and sensor components 42 of the sensor device 12. The capsule 34 is preferably designed with shapes that are easily accepted by the patient's body while minimizing patient discomfort. For example, the body of capsule 34 may be formed in a cylindrical shape with cylindrical sidewalls. Other non-cylindrical configurations may be employed, however, in which case the corners and edges may be designed with generous radii to present a capsule having smoothly contoured surfaces. In the depicted example, the body of capsule 34 is formed as a generally rectangular structure, which means that the outline of the shape of capsule 34 resembles a rectangle with the edges and corners that are contoured.

The capsule 34 is preferably formed having two sections 36, 38, one of which (36) can contain the sensing element 32, such as a pressure sensing diaphragm, of sensor device 12, while the other section (38) can contain the battery 40, and electronics and sensor components 42 of the sensor device 12.

The capsule 34 is formed from one or more biocompatible materials that can be hermetically sealed when the sections 36, 38 are joined. A number of such biocompatible materials may be employed, as will be understood by those familiar with the art, including metals and biocompatible plastics. For example, the sections 36, 38 may be formed from unalloyed titanium with an American Society for Testing and Materials (ASTM) grade 1 to grade 4 or an alloyed titanium (grade 5) that includes aluminum and vanadium. In some examples, section 36 may be formed from sapphire. For examples in which the sections are metal, the metal material of the capsule 34 may optionally be selected to be compatible with the fixation assembly 30 material so as to permit the fixation assembly 30 to be securely-coupled to the capsule 34. In other examples, the capsule 34 along with the fixation assembly 30 may be integrally formed from one or more of the same or distinct materials. In some examples, the capsule 34, as well as some portions of the fixation member 30, may be encapsulated in a biologically inert dielectric barrier material such as a film of silicone or polyp-xylylene) polymer sold under the trademark PARYLENE.

As shown in FIG. 4A, capsule 34 may include fasteners F1, F2 that define channels for reception of a segment of the fixation assembly 30. In the example of FIG. 4B, capsule 34 may include fasteners F3, F4 that define channels for reception of a segment of the fixation assembly 30. The received segment may include a portion along a length of the fixation assembly 30 or a free end of the fixation assembly 30. The fasteners F1-F4 are coupled to an exterior of the capsule 34, or in alternative examples, formed integrally with the capsule 34. For example, as shown in the example of FIG. 4A, the fasteners F1, F2 are provided at an exterior of the capsule 34 at the lateral sidewalls SW1, SW2, respectively. In the alternative example of FIG. 4B, the fasteners F3, F4 are provided at spaced apart locations on an exterior of one or more of the longitudinal walls of the capsule 34, such as the bottom longitudinal wall LW2.

In some examples, the fasteners are formed as pairs of tabs that are arranged to define one or more channel(s) for receiving one or more segment(s) of the fixation assembly 30. Each fastener can include a pair of tabs that are aligned longitudinally as described, for example, in U.S. Pat. No. 8,864,676 to Beasley et al. which is incorporated herein by reference in its entirety. The fasteners may be coupled to the capsule 34 through welding, for example. Alternatively, the fasteners may be formed integrally with the capsule 34, preferably on opposing ends of the capsule. However, the description of the fasteners F1-F4 is not intended to be limiting, and rather, it is provided to explain the context of the invention.

In the examples of FIGS. 4A-4B, the fasteners F1-F4 are formed as tubular structures that define channels that are sized to receive a segment of each of the fixation members 30A, 30B. In some examples, the fasteners F1-F4 may be formed as discrete components, such as tubes, for example, that can be coupled to the capsule 34 through coupling techniques such as welding or bonding agent such as glue or crimping. Alternatively, the fasteners may be formed integrally with the capsule 34. As will be described in more detail below, the fixation assembly 30 is coupled to the fasteners F1-F4 by any suitable coupling technique such as welding, crimping, bonding agent such as glue, frictional fit, etc.

The channels of fasteners F1-F4 may optionally be defined to receive a segment of the fixation members 30A, 30B in a snug fit arrangement to prevent relative movement between the capsule 34 and the fixation assembly 30. By way of dimensional example, the thickness of a cross section of fixation assembly 30 may be on the order of 0.006 inch for a round shape or 0.005 inch by 0.010 inch for a rectangular shape. In comparison, the diameter (or width) of the channel of each of the fasteners may be on the order of 0.010 inch to 0.025 inch.

The free ends of each of the fixation members 30A, 30B may be oriented in opposing directions. For example, a first of the free ends may be oriented downward in relation to the lateral sidewall SW1, SW2, while the other end may be oriented upward in relation to the lateral sidewalls SW1, SW2 as shown in FIG. 4A. Among other things, such an orientation can provide a degree of load cancellation that minimizes load transfer to the sensing element 32.

In alternative examples, one of the fixation members e.g., 30A may be coupled along a lateral sidewall such as SW1 as shown in FIG. 4A, and the other of the fixation members e.g., 30B may be coupled to a longitudinal wall such as LW1 or LW2 as shown in FIG. 4B.

Figure 5:
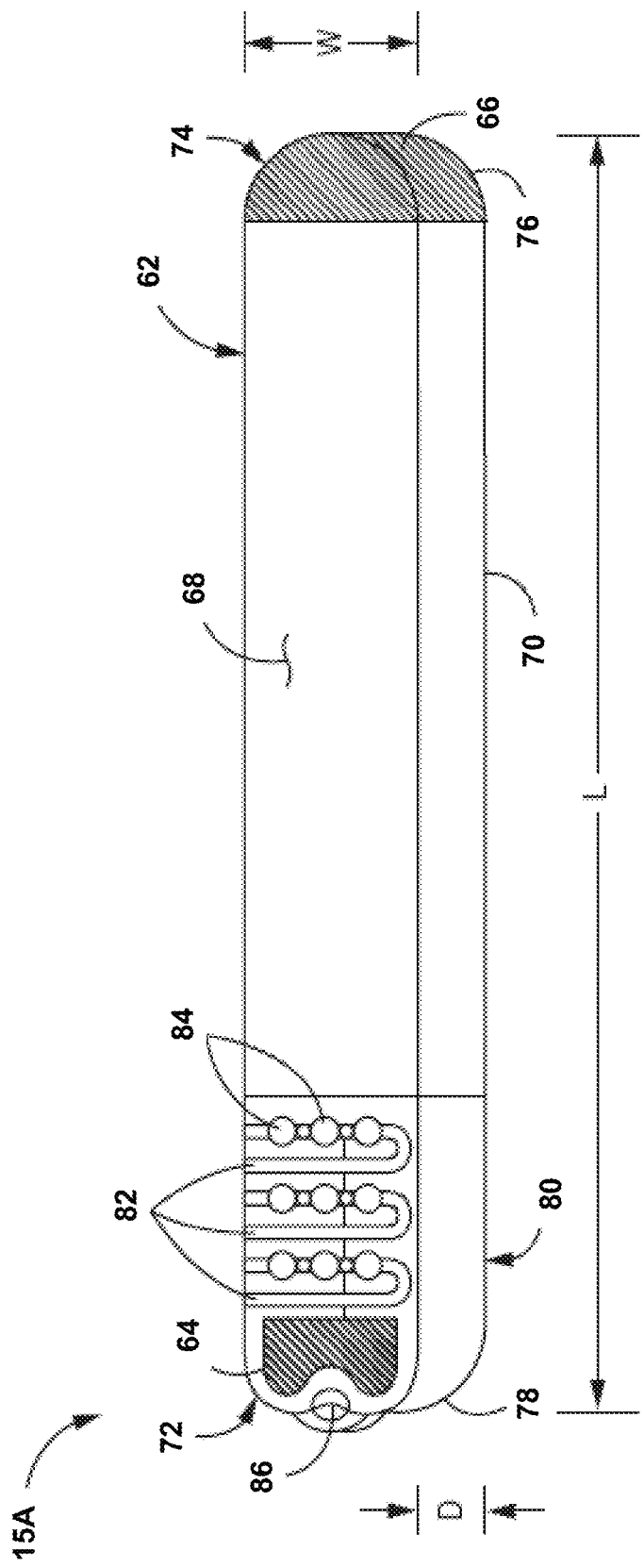
FIG. 5 is a conceptual drawing illustrating an example configuration of an insertable cardiac monitor.

FIG. 5 is a conceptual drawing illustrating an example configuration of ICM 15A of FIG. 1A. In the example shown in FIG. 5, ICM 15A may be embodied as a monitoring device having housing 62, proximal electrode 64 and distal electrode 66. Housing 62 may further comprise first major surface 68, second major surface 70, proximal end 72, and distal end 74. Housing 62 encloses electronic circuitry located inside the ICM 15A and protects the circuitry contained therein from body fluids. Electrical feedthroughs provide electrical connection of electrodes 64 and 66.

In the example shown in FIG. 5, ICM 15A is defined by a length L, a width W and thickness or depth D and is in the form of an elongated rectangular prism wherein the length L is much larger than the width W, which in turn is larger than the depth D. In one example, the geometry of the ICM 15A—in particular a width W greater than the depth D—is selected to allow ICM 15A to be inserted under the skin of the patient using a minimally invasive procedure and to remain in the desired orientation during insertion. For example, the device shown in FIG. 5 includes radial asymmetries (notably, the rectangular shape) along the longitudinal axis that maintains the device in the proper orientation following insertion. For example, in one example the spacing between proximal electrode 64 and distal electrode 66 may range from thirty millimeters (mm) to fifty-five mm, thirty-five mm to fifty-five mm, and from forty mm to fifty-five mm and may be any range or individual spacing from twenty-five mm to sixty mm. In addition, ICM 15A may have a length L that ranges from thirty mm to about seventy mm. In other examples, the length L may range from forty mm to sixty mm, forty-five mm to sixty mm and may be any length or range of lengths between about thirty mm and about seventy mm. In addition, the width W of major surface 68 may range from three mm to ten mm and may be any single or range of widths between three mm and ten mm. The thickness of depth D of ICM 15A may range from two mm to nine mm. In other examples, the depth D of ICM 15A may range from two mm to five mm and may be any single or range of depths from two mm to nine mm. In addition, ICM 15A according to an example of the present disclosure is has a geometry and size designed for ease of implant and patient comfort. Examples of ICM 15A described in this disclosure may have a volume of three cubic centimeters (cm) or less, one-and-a-half cubic cm or less or any volume between three and one-and-a-half cubic centimeters. In addition, in the example shown in FIG. 5, proximal end 72 and distal end 74 are rounded to reduce discomfort and irritation to surrounding tissue once inserted under the skin of the patient. In some examples, ICM 15A, including instrument and method for inserting ICM 15A is configured as described, for example, in U.S. Patent Publication No. 2014/0276928, incorporated herein by reference in its entirety. In some examples, ICM 15A is configured as described, for example, in U.S. Patent Publication No. 2016/0310031, incorporated herein by reference.

In the example shown in FIG. 5, once inserted within the patient, the first major surface 68 faces outward, toward the skin of the patient while the second major surface 70 is located opposite the first major surface 68. Consequently, the first and second major surfaces may face in directions along a sagittal axis of patient 2A (see FIG. 1), and this orientation may be consistently achieved upon implantation due to the dimensions of ICM 15A. Additionally, an accelerometer, or axis of an accelerometer, may be oriented along the sagittal axis.

Proximal electrode 64 and distal electrode 66 are used to sense cardiac signals, e.g. ECG signals, intra-thoracically or extra-thoracically, which may be sub-muscularly or subcutaneously. ECG signals may be stored in a memory of the ICM 15A, and ECG data may be transmitted via integrated antenna 82 to another medical device, which may be another implantable device or an external device, such as external device 14A. In some example, electrodes 64 and 66 may additionally or alternatively be used for sensing any biopotential signal of interest, which may be, for example, an EGM, electroencephalogram (EEG), electromyogram (EMG), or a nerve signal, from any implanted location.

In the example shown in FIG. 5, proximal electrode 64 is in close proximity to the proximal end 72 and distal electrode 66 is in close proximity to distal end 74. In this example, distal electrode 66 is not limited to a flattened, outward facing surface, but may extend from first major surface 68 around rounded edges 76 and/or end surface 78 and onto the second major surface 70 so that the electrode 66 has a three-dimensional curved configuration. In the example shown in FIG. 5, proximal electrode 64 is located on first major surface 68 and is substantially flat, outward facing. However, in other examples proximal electrode 64 may utilize the three-dimensional curved configuration of distal electrode 66, providing a three-dimensional proximal electrode (not shown in this example). Similarly, in other examples distal electrode 66 may utilize a substantially flat, outward facing electrode located on first major surface 68 similar to that shown with respect to proximal electrode 64. The various electrode configurations allow for configurations in which proximal electrode 64 and distal electrode 66 are located on both first major surface 68 and second major surface 70. In other configurations, such as that shown in FIG. 5, only one of proximal electrode 64 and distal electrode 66 is located on both major surfaces 68 and 70, and in still other configurations both proximal electrode 64 and distal electrode 66 are located on one of the first major surface 68 or the second major surface 70 (i.e., proximal electrode 64 located on first major surface 68 while distal electrode 66 is located on second major surface 70). In another example, ICM 15A may include electrodes on both major surface 68 and 70 at or near the proximal and distal ends of the device, such that a total of four electrodes are included on ICM 15A. Electrodes 64 and 66 may be formed of a plurality of different types of biocompatible conductive material, e.g. stainless steel, titanium, platinum, iridium, or alloys thereof, and may utilize one or more coatings such as titanium nitride or fractal titanium nitride.

In the example shown in FIG. 5, proximal end 72 includes a header assembly 80 that includes one or more of proximal electrode 64, integrated antenna 82, anti-migration projections 84, and/or suture hole 86. Integrated antenna 82 is located on the same major surface (i.e., first major surface 68) as proximal electrode 64 and is also included as part of header assembly 80. Integrated antenna 82 allows ICM 15A to transmit and/or receive data. In other examples, integrated antenna 82 may be formed on the opposite major surface as proximal electrode 64, or may be incorporated within the housing 62 of ICM 15A. In the example shown in FIG. 5, anti-migration projections 84 are located adjacent to integrated antenna 82 and protrude away from first major surface 68 to prevent longitudinal movement of the device. In the example shown in FIG. 5 anti-migration projections 84 includes a plurality (e.g., nine) small bumps or protrusions extending away from first major surface 68. As discussed above, in other examples anti-migration projections 84 may be located on the opposite major surface as proximal electrode 64 and/or integrated antenna 82. In addition, in the example shown in FIG. 5 header assembly 80 includes suture hole 86, which provides another means of securing ICM 15A to the patient to prevent movement following insert. In the example shown, suture hole 86 is located adjacent to proximal electrode 64. In one example, header assembly 80 is a molded header assembly made from a polymeric or plastic material, which may be integrated or separable from the main portion of ICM 15A.

Figure 6:
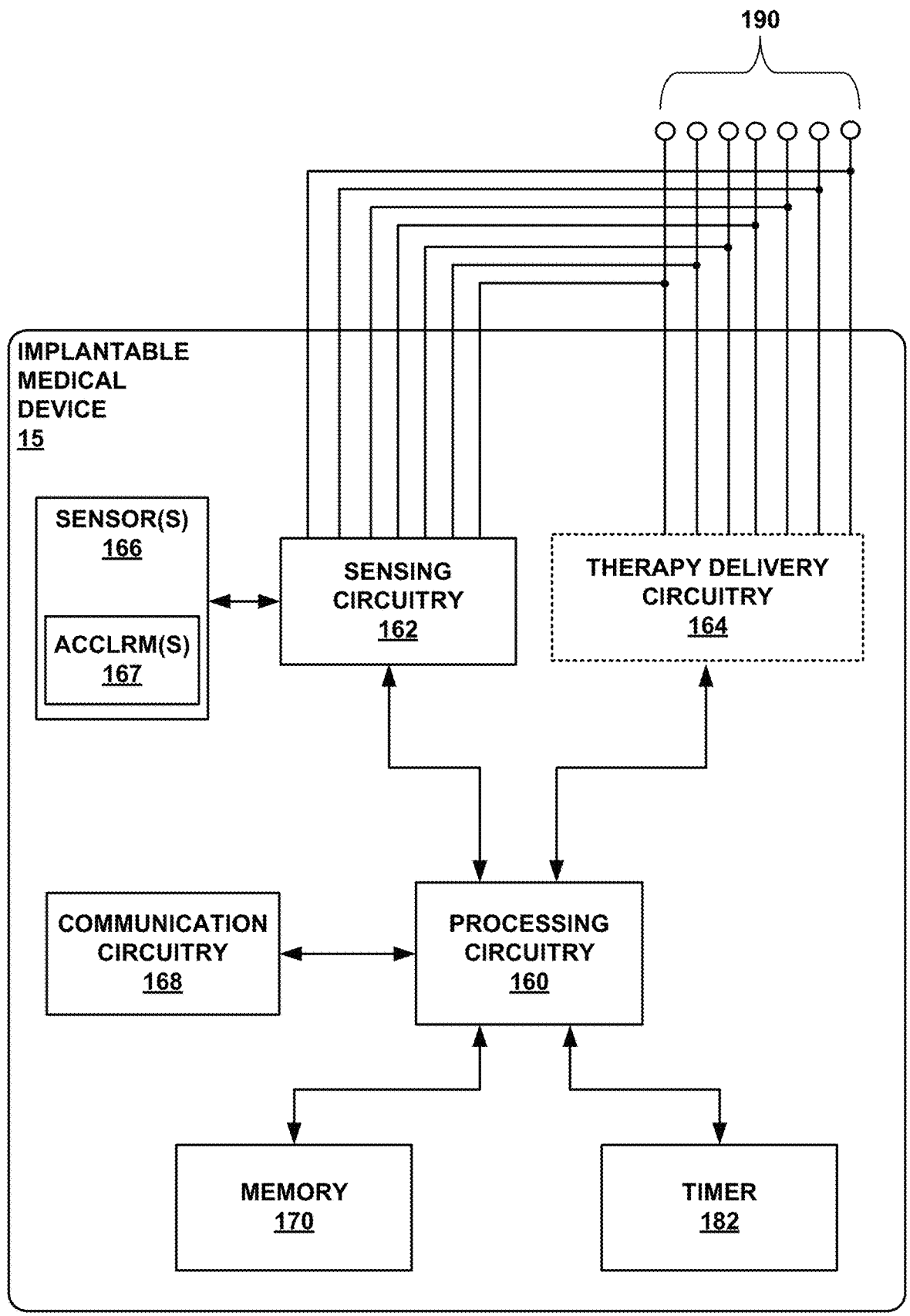
FIG. 6 is a functional block diagram illustrating an example configuration of an implantable medical device.

FIG. 6 is a functional block diagram illustrating an example configuration of an IMD 15. IMD 15 may correspond to ICM 15A in FIG. 1A and FIG. 5, IMD 15B in FIG. 1B, or another IMD configured to implement the techniques for determining whether to store or discard cardiovascular pressure measurements as described in this disclosure. In the illustrated example, IMD 15 includes processing circuitry 160 and an associated memory 170, sensing circuitry 162, therapy delivery circuitry 164, one or more sensors 166, and communication circuitry 168. However, an IMD 15 need not include all of these components, or may include additional components. For example, ICM 15A may not include therapy delivery circuitry 164, in some examples.

Memory 170 includes computer-readable instructions that, when executed by processing circuitry 160, cause IMD 15 and processing circuitry 160 to perform various functions attributed to IMD 15 and processing circuitry 160 herein (e.g., determining time of day, comparing time of day to a predetermined window, determining posture, comparing posture to target posture, and causing communication circuitry 168 to transmit cardiovascular pressure measurements to an external device). Memory 170 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 170 may store threshold(s) for time of day, posture, heart rate, activity level, respiration rate, and other parameters. Memory 170 may also store data indicating cardiovascular pressure measurements received from a sensor device 12.

Processing circuitry 160 may include fixed function circuitry and/or programmable processing circuitry. Processing circuitry 160 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 160 may include multiple components, such as any combination of one or more microprocessors, one or more controllers, one or more DSPs, one or more ASICs, or one or more FPGAs, as well as other discrete or integrated logic circuitry. The functions attributed to processing circuitry 160 herein may be embodied as software, firmware, hardware or any combination thereof.

Sensing circuitry 162 and therapy delivery circuitry 164 are coupled to electrodes 190. Electrodes 190 illustrated in FIG. 6 may correspond to, for example, electrodes carried on leads 18, 20, 22 of device 15B (FIG. 1B), or electrodes 64 and 66 of ICM 15A. Sensing circuitry 162 may monitor signals from a selected two or more of electrodes 190 in order to monitor electrical activity of heart, impedance, or other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 162 may include one or more filters and amplifiers for filtering and amplifying a signal received from electrodes 190. In some examples, sensing circuitry 162 may sense or detect physiological parameters, such as heart rate, blood pressure, respiration, and the like.

The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 162 outputs an indication to processing circuitry 160 in response to sensing of a cardiac event (e.g., detected P-waves or R-waves).

In this manner, processing circuitry 160 may receive detected cardiac event signals corresponding to the occurrence of detected R-waves and P-waves in the respective chambers of heart. Indications of detected R-waves and P-waves may be used for detecting ventricular and/or atrial tachyarrhythmia episodes, e.g., ventricular or atrial fibrillation episodes. Some detection channels may be configured to detect cardiac events, such as P- or R-waves, and provide indications of the occurrences of such events to processing circuitry 160, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Sensing circuitry 162 may also include a switch module to select which of the available electrodes 190 (or electrode polarities) are used to sense the heart activity. In examples with several electrodes 190, processing circuitry 160 may select the electrodes that function as sense electrodes, i.e., select the sensing configuration, via the switch module within sensing circuitry 162. Sensing circuitry 162 may also pass one or more digitized EGM signals to processing circuitry 160 for analysis, e.g., for use in cardiac rhythm discrimination.

In the example of FIG. 6, IMD 15 includes one or more sensors 166 coupled to sensing circuitry 162. Although illustrated in FIG. 6 as included within IMD 15, one or more of sensors 166 may be external to IMD 15, e.g., coupled to IMD 15 via one or more leads, or configured to wirelessly communicate with IMD 15. In some examples, sensors 166 transduce a signal indicative of a patient parameter, which may be amplified, filtered, or otherwise processed by sensing circuitry 162. In such examples, processing circuitry 160 determines values of patient parameters based on the signals. In some examples, sensors 166 determine the patient parameter values, and communicate them, e.g., via a wired or wireless connection, to processing circuitry 160.

In some examples, sensors 166 include one or more accelerometers 167, e.g., one or more three-axis accelerometers. Signals generated by the one or more accelerometers 167 may be indicative of, as examples, gross body movement (e.g., activity) of the patient, patient posture, heart sounds or other vibrations or movement associated with the beating of the heart, or coughing, rales, or other respiration abnormalities. Accelerometers 167 may produce and transmit signals to processing circuit 160 for a determination as to whether the patient is in a target posture during a measurement of cardiovascular pressure by a pressure sensing device. In some examples, sensors 166 include one or more microphones configured to detect heart sounds or respiration abnormalities, and/or other sensors configured to detect patient activity or posture, such as gyroscopes and/or strain gauges. In some examples, sensors 166 may include sensors configured to transduce signals indicative of blood flow, oxygen saturation of blood, or patient temperature, and processing circuitry 160 may determine patient parameters values based on these signals. Sensors 166 may gather data that includes numerical values or waveforms of patient parameters. In some examples, sensors 166 may sense a waveform of a patient's cardiovascular pressure. Data indicating the waveform may be stored in memory 170 and transmitted to another device through communication circuitry 168.

Therapy delivery circuitry 164 is configured to generate and deliver electrical therapy to the heart. Therapy delivery circuitry 164 may include one or more pulse generators, capacitors, and/or other components capable of generating and/or storing energy to deliver as pacing therapy, defibrillation therapy, cardioversion therapy, other therapy or a combination of therapies. In some instances, therapy delivery circuitry 164 may include a first set of components configured to provide pacing therapy and a second set of components configured to provide anti-tachyarrhythmia shock therapy. In other instances, therapy delivery circuitry 164 may utilize the same set of components to provide both pacing and anti-tachyarrhythmia shock therapy. In still other instances, therapy delivery circuitry 164 may share some of the pacing and shock therapy components while using other components solely for pacing or shock delivery.

Therapy delivery circuitry 164 may include charging circuitry, one or more charge storage devices, such as one or more capacitors, and switching circuitry that controls when the capacitor(s) are discharged to electrodes 190 and the widths of pulses. Charging of capacitors to a programmed pulse amplitude and discharging of the capacitors for a programmed pulse width may be performed by therapy delivery circuitry 164 according to control signals received from processing circuitry 160, which are provided by processing circuitry 160 according to parameters stored in memory 170. Processing circuitry 160 controls therapy delivery circuitry 164 to deliver the generated therapy to the heart via one or more combinations of electrodes 190, e.g., according to parameters stored in memory 170. Therapy delivery circuitry 164 may include switch circuitry to select which of the available electrodes 190 are used to deliver the therapy, e.g., as controlled by processing circuitry 160.

Memory 170 may store information relating to the predetermined window of time for cardiovascular pressure measurements. Memory 170 may also store data related to cardiovascular pressure measurements, such as the pressure values, pressure waveforms, and the corresponding times of day and patient postures. Memory 170 may also store information relating to the target posture for cardiovascular pressure measurements, such as thresholds for signals from accelerometers 167.

Processing circuitry 160 may determine the time of day using timer 182. Timer 182 may be keep a running count based on a voltage-controller oscillator or any other suitable oscillator or clock. Timer 182 may generate an alert to processing circuitry 160 when the time of day is within the predetermined window of time for cardiovascular pressure measurements.

Communication circuitry 168 includes any suitable hardware, firmware, software or any combination thereof for communicating with another device, such as an external device 14 or another IMD or sensor. Under the control of processing circuitry 160, communication circuitry 168 may receive downlink telemetry from and send uplink telemetry to an external device 14 or another device with the aid of an antenna, which may be internal and/or external. In some examples, communication circuitry 168 may communicate with a local external device, and processing circuitry 160 may communicate with a networked computing device via the local external device and a computer network, such as the Medtronic CareLink® Network developed by Medtronic, plc, of Dublin, Ireland.

A clinician or other user may retrieve data from IMD 15 using external device 14 or another local or networked computing device configured to communicate with processing circuitry 160 via communication circuitry 168. The clinician may also program parameters of IMD 15 using external device 14 or another local or networked computing device. In some examples, the clinician may select times of day and target posture(s) for cardiovascular pressure measurements.

Communication circuitry 168 may also be configured to communicate with an implantable pressure sensing device 12. Processing circuitry 160 may receive measured cardiovascular pressure values, e.g., PAP values, from pressure sensing device 12 via communication circuitry 168. In some examples, processing circuitry 160 may send a trigger signal to sensing device 12 via communication circuitry 168 to control the sensing device to measure cardiovascular pressure in response to the trigger signal.

Although not illustrated in FIG. 6, communication circuitry 168 may be coupled or coupleable to electrodes 190 for tissue conductance communication (TCC) via the electrodes. In some examples, communication with sensor device 12 and external device 14 may be via RF telemetry or TCC. In one example, communication circuitry 168 may be configured for RF telemetry communication with external device 14 and TCC with sensor device 12

Figure 7:
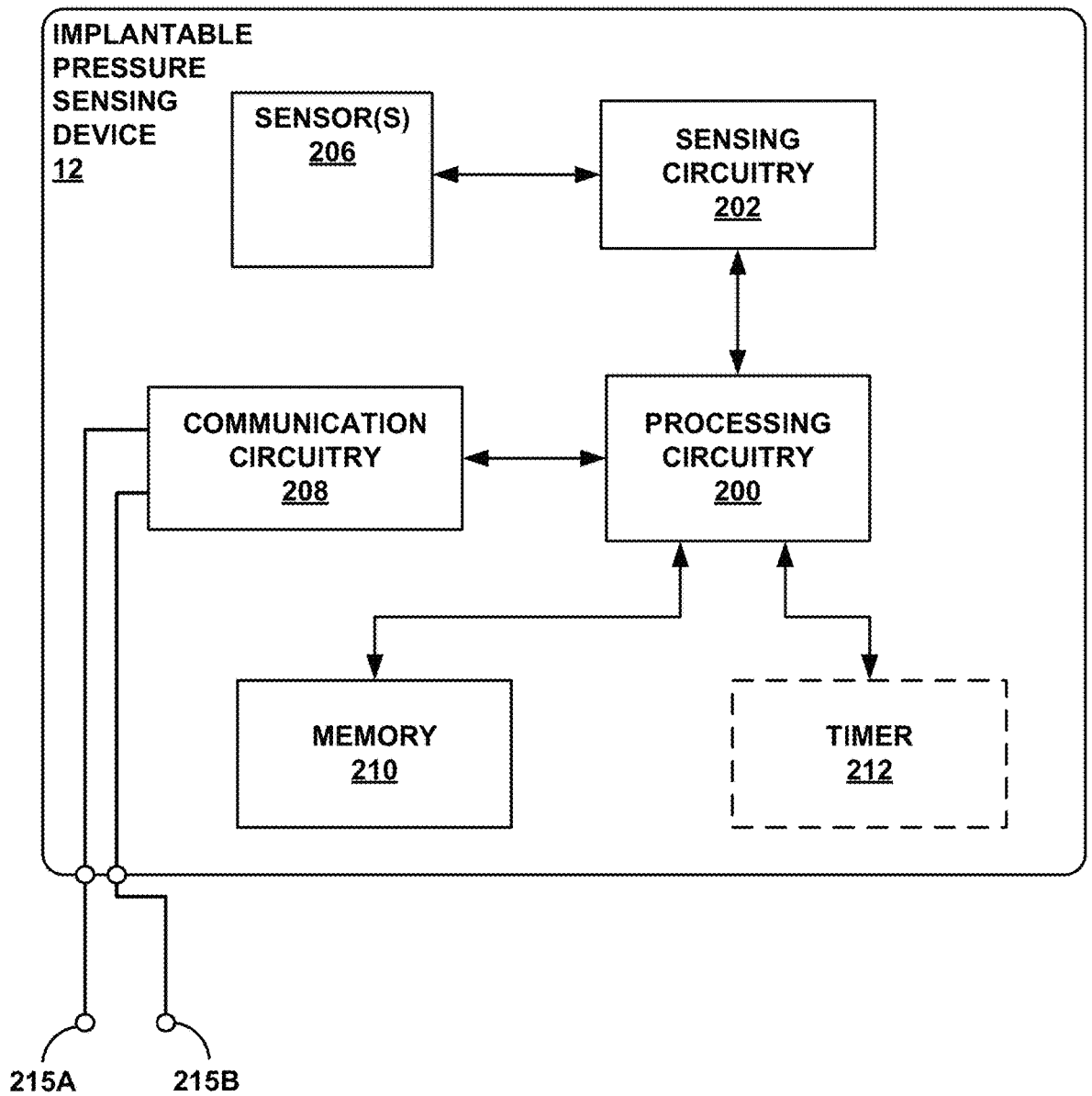
FIG. 7 is a functional block diagram illustrating an example configuration of implantable pressure sensing device.

FIG. 7 is a functional block diagram illustrating an example configuration of implantable pressure sensing device 12, hereinafter called "sensor 12" or "sensing device 12." Sensing device 12 may correspond to any of sensor device 12A in FIG. 1A, sensor device 12B in FIG. 1B, sensor device 12 in FIGS. 2A-2B, or another pressure sensing device configured to implement the techniques for measuring cardiovascular pressure as described in this disclosure. In the illustrated example, sensing device 12 includes processing circuitry 200 and an associated memory 210, sensing circuitry 202, one or more sensors 206, communication circuitry 208, and an optional timer 212. However, sensing device 12 need not include all of these components, or may include additional components.

Memory 210 includes computer-readable instructions that, when executed by processing circuitry 200, cause sensing device 12 and processing circuitry 200 to perform various functions attributed to sensing device 12 and processing circuitry 200 herein (e.g., determining time of day, comparing time of day to a predetermined window, causing communication circuitry 208 to receive triggering signals from another device, causing communication circuitry 208 to transmit cardiovascular pressure measurements to the other device). Memory 210 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 210 may store threshold(s) for time of day and other parameters. Memory 210 may also store data indicating cardiovascular pressure measurements.

Processing circuitry 200 may include fixed function circuitry and/or programmable processing circuitry. Processing circuitry 200 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 200 may include multiple components, such as any combination of one or more microprocessors, one or more controllers, one or more DSPs, one or more ASICs, or one or more FPGAs, as well as other discrete or integrated logic circuitry. The functions attributed to processing circuitry 200 herein may be embodied as software, firmware, hardware or any combination thereof.

Sensing circuitry 202 may monitor signals from sensors 206, which may include pressure sensors. In some examples, sensing circuitry 202 may sense or detect physiological parameters such as blood pressure in the cardiovascular system of a patient. In some examples, sensing device 12 may be implanted in a pulmonary artery of the patient.

In some examples, sensors 206 include one or more pressure sensors that transduce one or more signals indicative of blood pressure, and processing circuitry 200 determines one or more patient parameter values based on the pressure signals. A capacitive pressure sensor is one example of a sensor for transducing pressure. Other example pressure sensors include piezoresistive, piezoelectric, electromagnetic, or optical pressure sensors. Patient parameter values determined based on pressure may include, as examples, systolic or diastolic pressure values, such as pulmonary artery diastolic pressure values, or other pulmonary artery pressure values.

Communication circuitry 208 includes any suitable hardware, firmware, software or any combination thereof for communicating with another device, such as IMD 15 or another IMD or sensor, or external device 14. In some examples, communication circuitry 208 may communicate with a local external device, and processing circuitry 200 may communicate with a networked computing device via the local external device and a computer network, such as the Medtronic CareLink® Network developed by Medtronic, plc, of Dublin, Ireland. In the illustrated example, communication circuitry 208 is coupled to electrodes 215A and 215B and configured for TCC communication, e.g., with IMD 15, via the electrodes. In some examples, electrodes 215A and 215B may be integral with a housing of implantable pressure sensing device 12, and/or may take the form of one or more of the fixation elements, e.g., fixation elements 30, of an implantable sensor assembly 10. In some examples, communication circuitry 208 may additionally or alternatively be configured for RF communication via an antenna (not shown).

Communication circuitry 208 may be configured to receive a triggering signal from another device, e.g., IMD 15. The triggering signal may cause processing circuitry 200 to control sensing circuitry 202 and sensor(s) 206 to transduce a cardiovascular pressure signal to measure cardiovascular pressure. Communication circuitry 208 may be further configured to transmit the cardiovascular pressure measurements and/or a portion of the pressure signal waveform to another device, e.g., IMD 15.

Processing circuitry 200 may determine the time of day using and optional timer 212. Optional timer 212 may be keep a running count based on a voltage-controller oscillator or any other suitable oscillator or clock. Optional timer 212 may generate an alert to processing circuitry 200 when the time of day is within the predetermined window of time for cardiovascular pressure measurements. In some examples, the determination of the time of day may include determining whether the time falls within a predetermined window.

Figure 8:
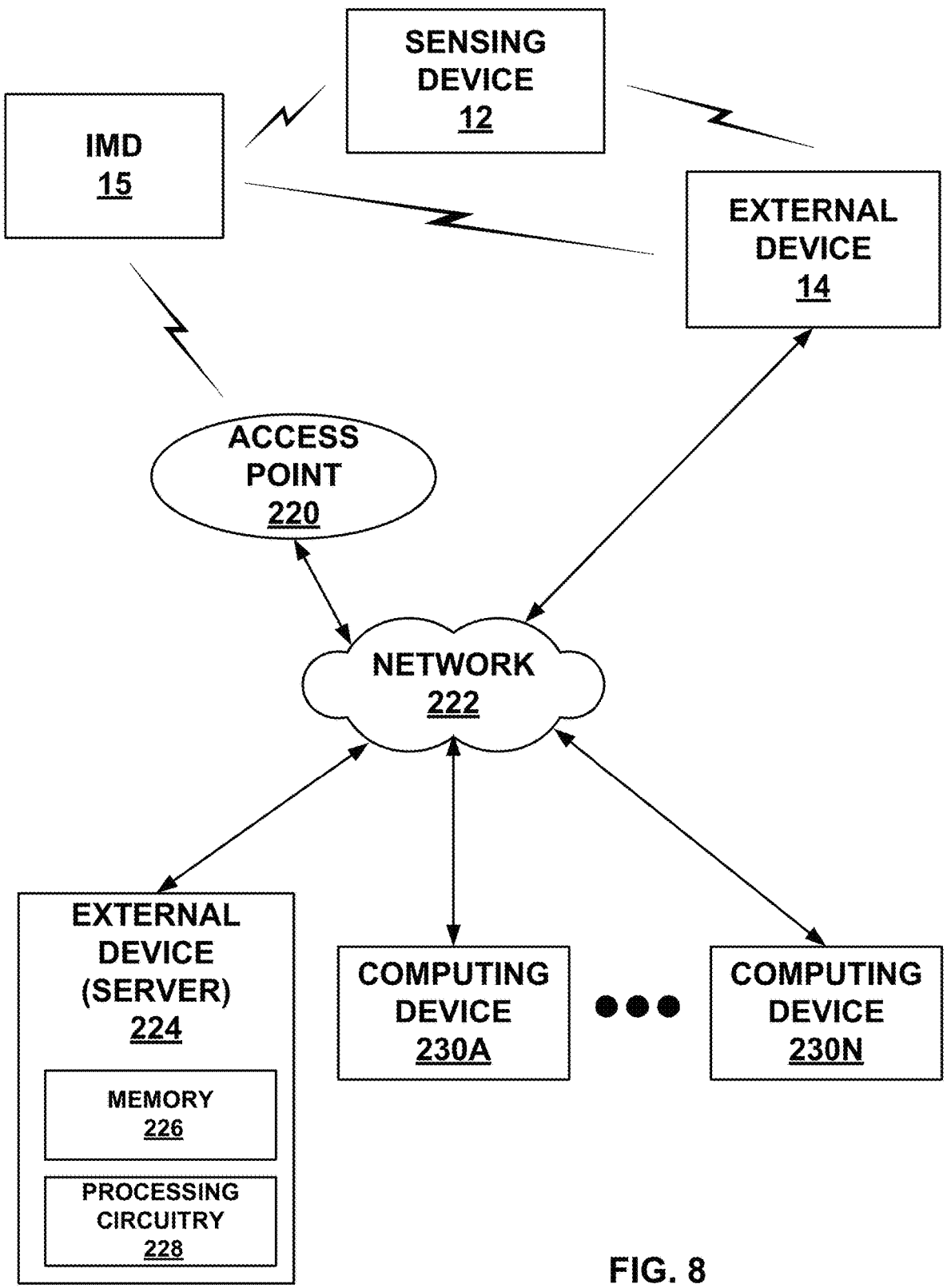
FIG. 8 is a functional block diagram illustrating an example system that includes external computing devices.

FIG. 8 is a functional block diagram illustrating an example system that includes external computing devices, such as a server 224 and one or more other computing devices 230A-230N, that are coupled to IMD 15, sensing device 12, and external device 14 via a network 222. In this example, IMD 15 may use its communication module 168 to, e.g., at different times and/or in different locations or settings, communicate with external device 14 via a first wireless connection, and to communication with an access point 220 via a second wireless connection. In the example of FIG. 8, access point 220, external device 14, server 224, and computing devices 230A-230N are interconnected, and able to communicate with each other, through network 222.

Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with the patient. Access point 220 may interrogate IMD 15, e.g., periodically or in response to a command from the patient or network 222, to retrieve cardiovascular pressure measurements, corresponding times of day, corresponding posture data, and/or other operational or patient data from IMD 15. Access point 220 may provide the retrieved data to server 224 via network 222.

In some cases, server 224 may be configured to provide a secure storage site for data that has been collected from IMD 15, sensing device 12, and/or external device 14. In some cases, server 224 may assemble data in web pages or other documents for viewing by trained professionals, such as clinicians, via computing devices 230A-230N. The illustrated system of FIG. 8 may be implemented, in some aspects, with general network technology and functionality similar to that provided by the Medtronic CareLink® Network developed by Medtronic plc, of Dublin, Ireland.

In some examples, one or more of access point 220, server 224, or computing devices 230 may be configured to perform, e.g., may include processing circuitry configured to perform, some or all of the techniques described herein, e.g., with respect to processing circuitry 160 of IMD 15 and processing circuitry 200 of external device 14, relating to cardiovascular pressure measurements. In the example of FIG. 8, server 224 includes a memory 226 to store cardiovascular pressure measurements, along with corresponding data such as time of day, posture, heart rate, activity level, and respiration rate, received from IMD 15 and/or external device 14, and processing circuitry 228, which may be configured to provide some or all of the functionality ascribed to processing circuitry 160 of IMD 15 and processing circuitry 200 of external device 14 herein. For example, processing circuitry 228 may determine whether the measured posture from one or more IMDs 15 was a target posture for cardiovascular pressure measurements. Processing circuitry 228 may determine whether to store or discard the cardiovascular pressure measurement based on determining whether the measured posture was the target posture.

Figure 9:
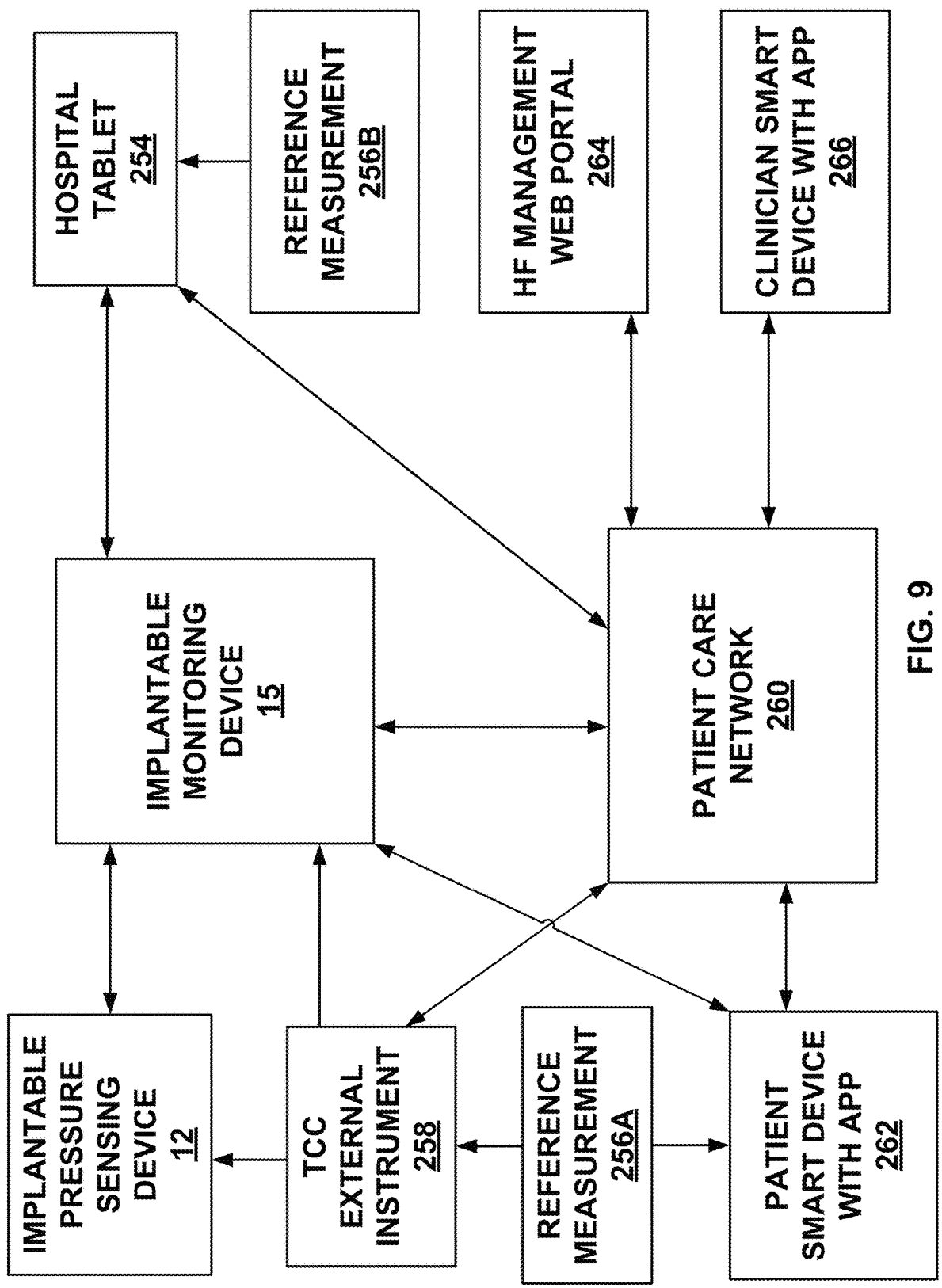
FIG. 9 is a block diagram illustrating another example system that includes external computing devices.

FIG. 9 is a block diagram illustrating another example system that includes external computing devices, such as hospital tablet 254, TCC external instrument 258, patient smart device 262, clinician smart device 266. Implantable pressure sensing device 12 may correspond to any of sensor device 12A in FIG. 1A, sensor device 12B in FIG. 1B, sensor device 12 in FIGS. 2A-2B, sensing device 12 in FIGS. 7 and 8, or another pressure sensing device configured to implement the techniques for measuring cardiovascular pressure as described in this disclosure. Implantable monitoring device (IMD) 15 may correspond to any of ICM 15 in FIG. 1A, device 15B in FIG. 1B, IMD 15 in FIG. 5, IMD 15 in FIG. 6 or 8, or another IMD configured to implement the techniques for determining whether to store or discard cardiovascular pressure measurements as described in this disclosure. In the example depicted in FIG. 9, IMD 15 may include communication links with implantable pressure sensing device 250, hospital tablet 254, TCC external instrument 258, patient care network 260, and patient smart device 262.

The system of FIG. 9 may notify a patient or clinician of a cardiovascular pressure measurement through one or more devices. For example, TCC external instrument 258 may communicate with IMD 15 and/or implantable pressure sensing device 12 via tissue conductive communications (TCC) through the body tissue of the patient. One or both of TCC external instrument 258 and patent smart device 262 may include reference measurement 256A, which may be a measurement of local air pressure to calibrate or adjust the cardiovascular pressure measurements taken by implantable pressure sensing device 12. Although reference measurement 256A is depicted as a single measurement, each of TCC external instrument 258 and patent smart device 262 may include or communicate with a separate reference measurement device.

Hospital tablet 254 and patient care network 260 may communicate with IMD 15 via radio frequency (RF) waves or TCC. Hospital tablet 254 may include reference measurement 256B, which may be the same or a separate reference measurement device as reference measurement 256A. A patient or clinician may use hospital tablet 254 or TCC external instrument 258 to obtain measurements and/or determine medication instructions.

Patient care network 260 may include a communication links with hospital tablet 254, TCC external instrument 258, patient smart device 262, HF management web portal 264, and clinician smart device 266. As a result, a clinician may access a patient's cardiovascular pressure measurements through hospital tablet 254 or clinician smart device 266 when the patient is in the hospital. A clinician may access a patient's cardiovascular pressure measurements through clinician smart device 266 when the patient is not in the hospital if IMD 15 has a remote communication link with patient care network 260. One or more of hospital tablet 254, TCC external instrument 258, patient smart device 262, and clinician smart device 266 may output instructions to a clinician or a patient. In some examples, a device of FIG. 9 may instruct a patient to take blood-pressure medication based on elevated cardiovascular pressure measurements taken by implantable pressure sensing device 12. A device that displays medication instructions may communicate with patient care network 260 to determine the medication instructions to display to a patient. A device of FIG. 9 may generate an alert to a clinician or patient based on abnormal or unhealthy cardiovascular pressure measurements.

Figure 10:
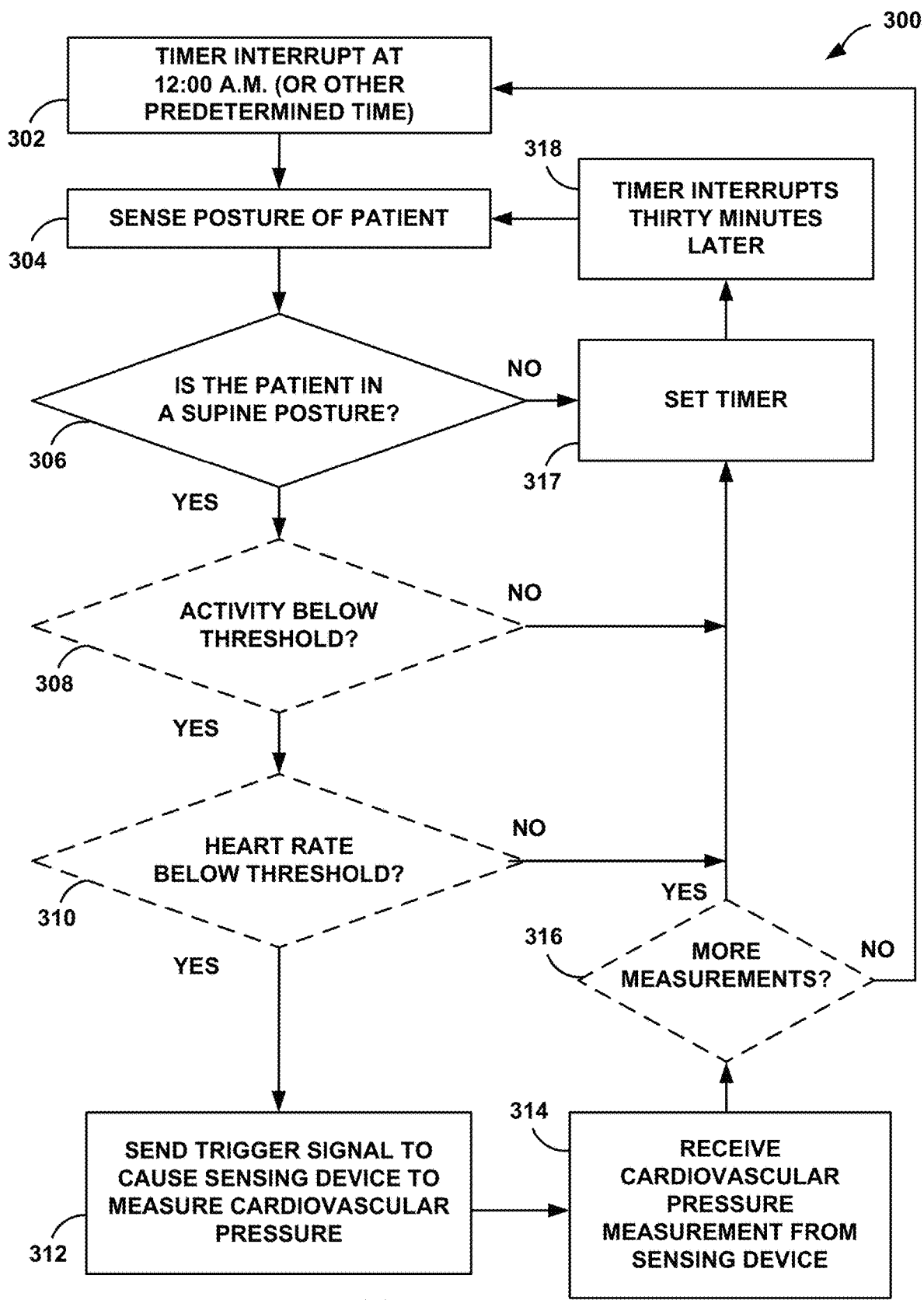
FIG. 10 is a flowchart illustrating an example technique that may be implemented by implantable medical device, in accordance with this disclosure.

FIG. 10 is a flowchart illustrating an example technique 300 that may be implemented by an IMD 15 in accordance with this disclosure. Technique 300 may be a specific example of technique 280. Technique 300 may be implemented by any one of the implantable medical devices (IMDs) discussed above because each one of the IMDs is configured to include at least one accelerometer (i.e., accelerometer circuitry), as well as communication and processing circuitry (see FIG. 6 and corresponding description) to facilitate determining patient movements.

The technique of FIG. 10 includes a timer interrupt at midnight, twelve a.m., or another predetermined time of day (302). Midnight may be a predetermined time because of the likelihood that the patient is sleeping and/or lying down at midnight. In some examples, IMD 15 may store more than one predetermined time, such as eight or nine times from midnight through four a.m. local time. By using a predetermined time window, patients and clinicians may obtain automatic measurements without needing to arrange for a measurement during the day. Therefore, using a predetermined tine window may increase compliance by the patient.

The technique of FIG. 10 further includes sensing the posture of the patient (304). IMD 15 may use sensing circuitry 162, sensors 166, and accelerometers 167 to generate and transmit signals indicating the posture to processing circuitry 160. IMD 15 may include three accelerometers, where each accelerometer may measure the orientation of the patient along one of three axes, such as longitudinal, transverse, and sagittal.

The technique of FIG. 10 further includes determining whether the patient is in a supine posture (306). Memory 170 may store data relating to threshold values for one or more accelerometer signals indicating that the patient is within the supine position. Processing circuitry 160 may compare the stored data relating to the target posture to the measured accelerometer signals. When the patient is in a supine posture, the pulmonary artery may include a hydrostatic column of blood of two or three inches above the pressure sensing device. When the patient is lying on the right side, the hydrostatic column of blood may decrease to one or two inches if the pressure sensing device is located on left side of the patient's thorax. Thus, the cardiovascular pressure measurement may decrease when the patient is lying on the right side, as compared to the supine posture, because there is less blood on top of the sensor. In contrast, when the patient is lying on the left side, the hydrostatic column of blood may increase to ten or twelve inches. For this reason, the cardiovascular pressure measurement may increase when the patient is lying on the left side, as compared to the supine posture. Furthermore, other postures such as standing or sitting may affect cardiovascular pressure measurements.

The supine position may be the target posture to ensure that all measurements have the same posture. For patients that sleep on their side, another posture may be used as the target posture, such as the right-supine posture. In some examples, the target posture may include multiple postures, and memory 170 may store each cardiovascular pressure measurement along with data indicating the corresponding posture. By including storing data for cardiovascular pressure measurements in a single or small group of postures, the cardiovascular pressure measurements may have been measured under the same or similar conditions and compared to each other in a meaningful way.

In some examples, the technique of FIG. 10 further includes determining if the activity level of the patient is below a threshold (308). A high activity level of the patient may significantly affect the cardiovascular pressure of the patient. By filtering out times with high activity levels, the technique of FIG. 10 may gather a more homogenous set of data. Processing circuitry 160 of IMD 15 may determine the activity level of patient based on one or more of the accelerometer signals, e.g., by comparing the accelerometer signals to one or more thresholds and/or counting threshold-crossings, zero-crossings, or inflections.

In some examples, the technique of FIG. 10 further includes determining if the heart rate of the patient is below a threshold (310). A high heart rate may indicate a stressful event or some other occurrence that may also raise the cardiovascular pressure of the patient. By filtering out times with high heart rates, the technique of FIG. 10 may gather a more homogenous set of data.

The technique of FIG. 10 further includes sending a trigger signal to cause a sensing device to measure cardiovascular pressure (312). IMD 15 may send the trigger signal via TCC or RF to the sensing device, which may be implanted in the vascular system of the patient.

The technique of FIG. 10 further includes receiving the cardiovascular pressure measurement from the sensing device (314). IMD 15 may receive the cardiovascular pressure measurement as a signal via TCC or RF from the sensing device. IMD 15 may store the cardiovascular pressure measurement to memory 170 before sending the cardiovascular pressure measurement to an external device. In some examples, the sensing device may transmit the cardiovascular pressure measurement directly to an external device.

In some examples, the technique of FIG. 10 further includes determining whether a desired number measurements, which may be a programmable number, have been taken (316). If IMD 15 determines that a sufficient number of measurements have been taken, IMD 15 may wait until the following night to request measurements from the sensing device. If IMD 15 determines that an insufficient number of measurements have been taken, IMD 15 may request an additional measurement from sensing device when IMD 15 determines that the posture of the patient is the target posture. In this way, IMD 15 may continue to request additional measurements until there are a sufficient number of measurements for a particular period of time. In counting the number of measurements, IMD 15 may count the stored measurements and not count the discarded measurements.

The technique of FIG. 10 further includes setting a timer (317). The timer may be set for a specific amount of time, such as thirty minutes. If the previous posture measurement did not match the target posture, the timer may be set for a shorter period of time to allow for additional measurements.

The technique of FIG. 10 further includes sensing the posture of the patient when the timer interrupts thirty minutes later (304, 318). The timer interrupt may be a shorter amount of time if the previous posture measurement did not match the target posture.

Figure 11:
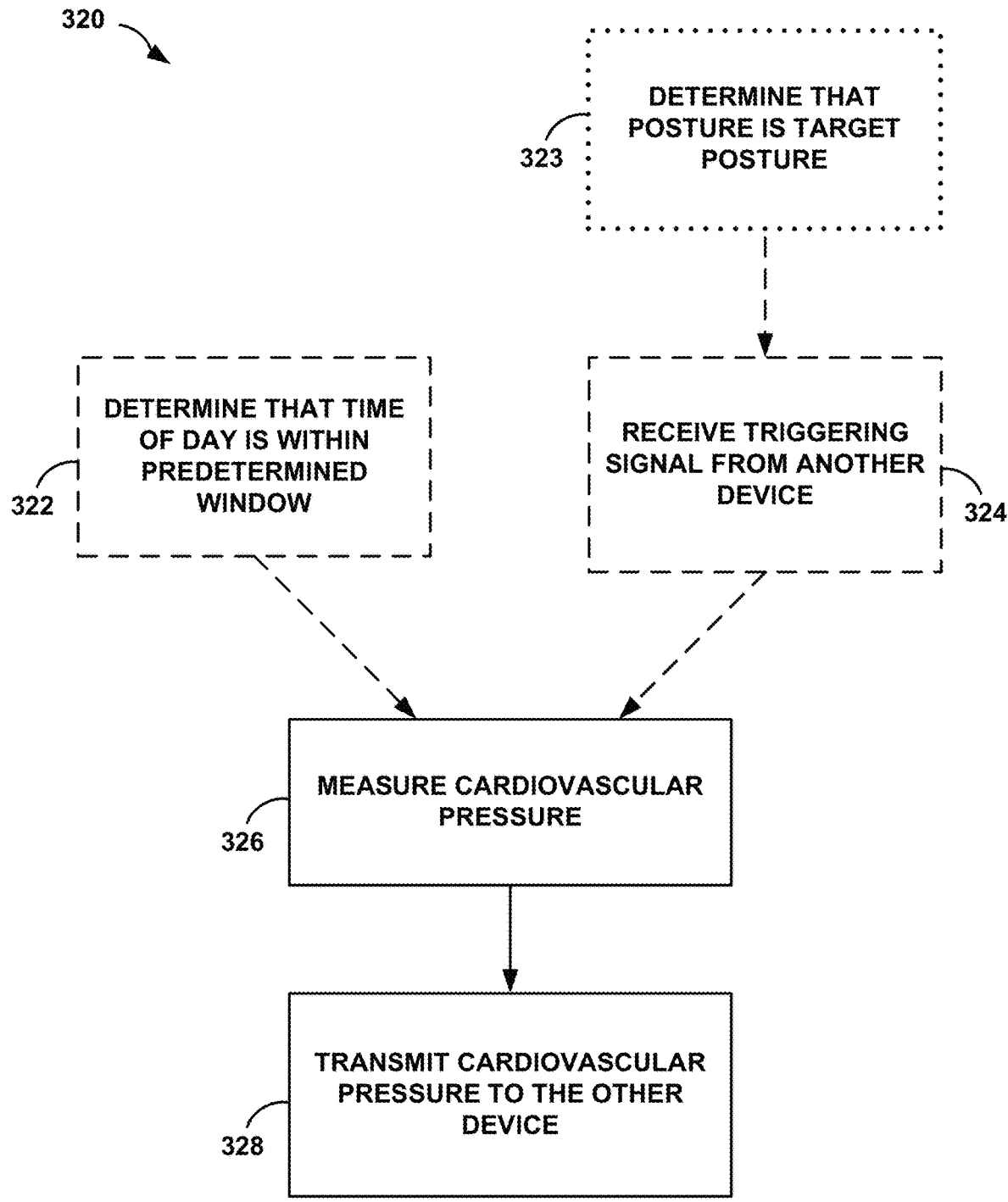
FIG. 11 is a flowchart illustrating an example technique that may be implemented by an implantable pressure sensing device, in accordance with this disclosure.

FIG. 11 is a flowchart illustrating an example technique 320 that may be implemented by sensor device 12 in FIGS. 1A-4B, and/or implantable pressure sensing device 12 in FIGS. 7-9, in accordance with this disclosure. Technique 320 may be a specific example of technique 280. Technique 320 may be implemented by any one of the sensing devices discussed above.

In some examples, the technique of FIG. 11 optionally includes sensor device 12 determining that the time of day is within a predetermined window (322). In some examples, an implantable monitoring device such as IMD 15 and/or an implantable pressure sensing device such as sensor device 12A may determine whether the time of day is within the predetermined window, e.g., during a period of time in which a patient is likely to be asleep, such as from midnight to 4 am. Either device may determine the time using a timer based on a voltage-controlled oscillator within the device. The device may compare the current time to a predetermined time or window of time. In some examples, the device may have previously set a timer and established an interrupt sequence such that processing circuitry within the device will begin executing instructions in the interrupt sequence in response to the timer reaching a threshold that corresponds to a predetermined time. Alternatively or additionally, sensor device 12 may receive a triggering signal from another device (324). The triggering signal may be based on the other device determining that the posture of the patient is a target posture (323). In either step of the technique of FIG. 11, sensor device 12 is triggered to measure the cardiovascular pressure of the patient. In some examples, sensor device 12 may or may not include an internal clock/timer for tracking the time of day.

The technique of FIG. 11 further includes measuring the cardiovascular pressure of the patient (326). A device such as implantable pressure sensing device 201 may use sensing circuitry 202 and sensor(s) 206 to measure the blood pressure in the vascular system of a patient. The sensing device may use sensing circuitry 202 and sensors 206 for generating, processing, and storing signals indicating the cardiovascular pressure of the patient. The device may measure the cardiovascular pressure in response to a program instruction, a timer interrupt, a triggering signal, a posture measurement, and/or any other suitable trigger or stimulus. In some examples, the device may take the measurement in response to determining that the time of day is within the predetermined window.

The technique of FIG. 11 further includes transmitting the cardiovascular pressure measurement to another device (328). Sensor device 12 may transmit the cardiovascular pressure measurement via TCC to IMD 15, which may be implanted subcutaneously near the sternum. IMD 15 may include more complex communication circuitry for transmitting the cardiovascular pressure measurement to an external device. In some examples, implantable pressure sensing device 12 may use communication circuitry 208 to transmit the cardiovascular pressure measurement to IMD 15. IMD 15 may receive the cardiovascular pressure measurement through communication circuitry 168. The cardiovascular pressure measurement may be transmitted between devices by radio frequency via an antenna or by TCC.

Figure 12:
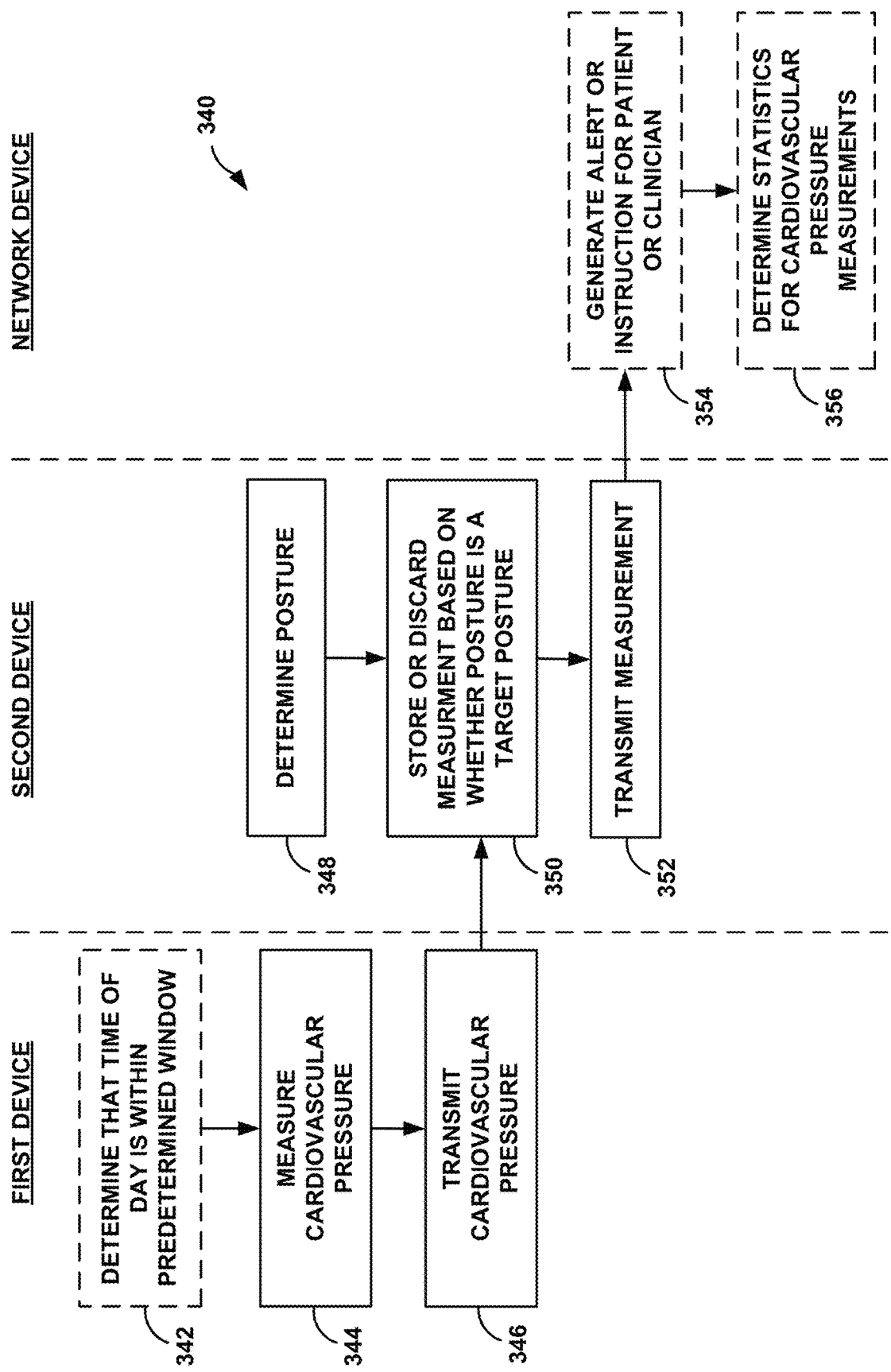
FIG. 12 is a flowchart illustrating an example technique that may be implemented by devices of a medical device system, in accordance with this disclosure.

FIG. 12 is a flowchart illustrating an example technique 340 that may be implemented by devices of a medical device system, in accordance with this disclosure. Technique 340 may be a specific example of technique 280. Technique 340 may be implemented by three or more devices, or by fewer than three devices by combining the functions of two devices into a single device. The division of labor depicted in FIG. 12 may be based on the larger battery and higher number of sensors in the second device compared to the first device. The first device may be configured for implantation in the cardiovascular system of the patient. Thus, the first device may be smaller than the second device.

The first device of FIG. 12 may be a pressure sensing device configured to determine that the time of day is within a predetermined window (342). The pressure sensing device may then measure the cardiovascular pressure of the patient (344). The pressure sensing device may transmit the cardiovascular pressure to a second device (346). The first device may be implemented by sensor device 12 in FIGS. 1A-4B, and/or implantable pressure sensing device 12 in FIGS. 7-9.

The second device of FIG. 12 may be a monitoring device or a hub device configured to determine a posture of the patient (348). The monitoring device may then store or discard the cardiovascular pressure measurement based on the determination of whether the posture is the target posture (350). If the monitoring device stores the cardiovascular pressure measurement, the monitoring device may transmit the stored cardiovascular pressure measurement to a network device (352). The second device may be implemented by IMD 15 in FIGS. 1A-8, device 15B in FIG. 1B, and/or IMD 15 in FIG. 9. In some examples, the second device may transmit all cardiovascular pressure measurements to the network device, along with the corresponding postures, and the network device may store, discard, process, and/or analyze the cardiovascular pressure measurements.

The network device of FIG. 12 may be configured to generate an alert or instruction for the patient or clinician (354). The network device may instruct a patient to take medication for high blood pressure, or cease taking the medication if the measurement indicates low blood pressure. The network device may be further configured to determine statistics for cardiovascular pressure measurements (356). The network device may be implemented by hospital tablet 254, TCC external instrument 258, patient smart device 262, or clinician smart device 266.

Figure 13:
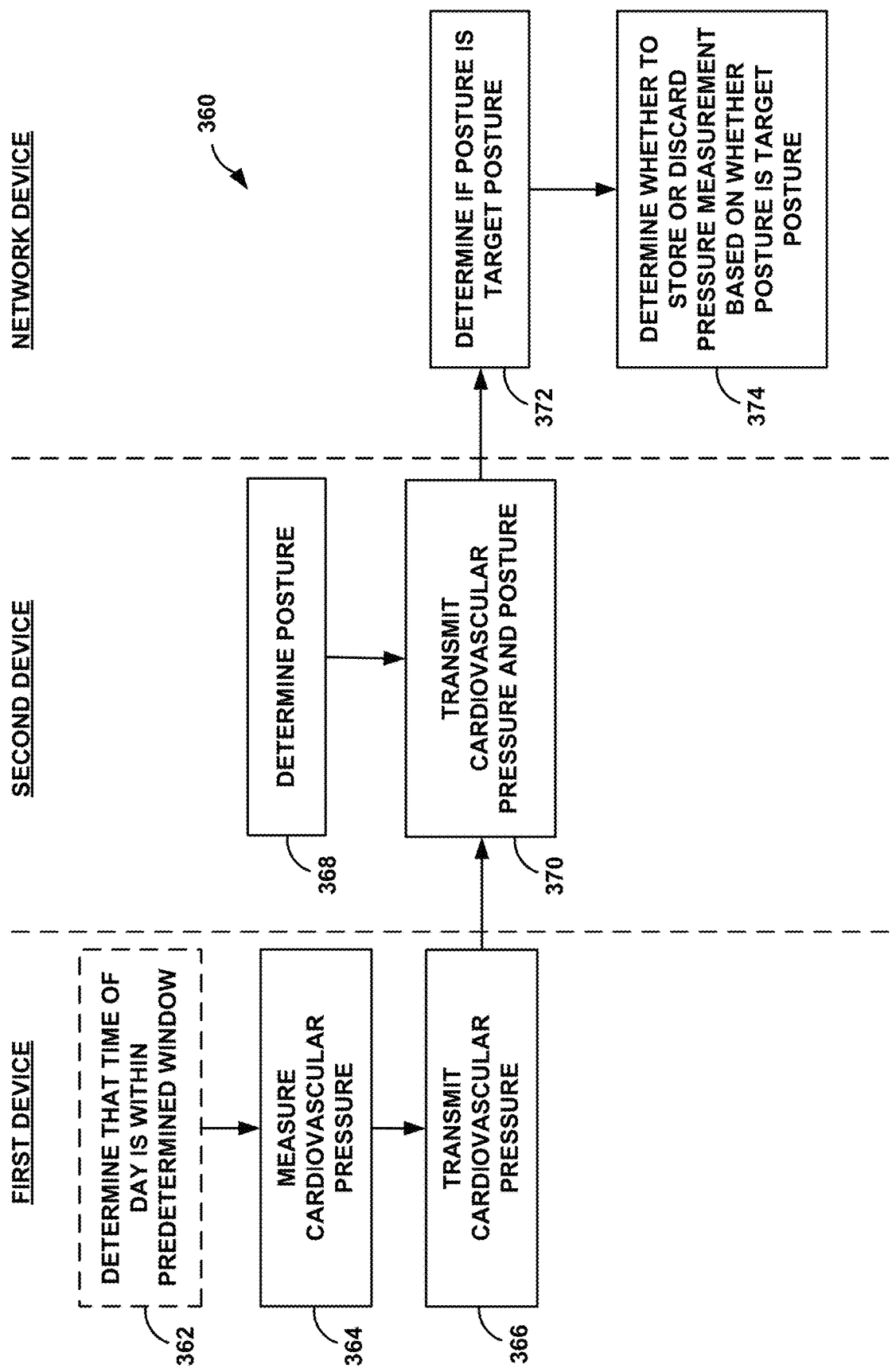
FIG. 13 is a flowchart illustrating an example technique that may be implemented by devices of a medical device system, in accordance with this disclosure.

FIG. 13 is a flowchart illustrating an example technique 360 that may be implemented by a pressure sensing device and a monitoring device, in accordance with this disclosure. Technique 360 may be a specific example of technique 280. The first device may be implemented by IMD 15 in FIGS. 1A-8, device 15B in FIG. 1B, and/or IMD 15 in FIG. 9. The second device may be implemented by sensor device 12 in FIGS. 1A-4B and/or implantable pressure sensing device 12 in FIGS. 7-9.

The pressure sensing device may be configured to operate in a low-power mode such as sleep mode or idle mode until waking up based on a triggering signal or internal timer interrupt. In some examples, the first device may determine that the time of day is within a predetermined window (362) and measure and optionally store the cardiovascular pressure of the patient (364). The first device may then transmit the pressure measurement to the second device (366). The second device may be configured to determine the posture of the patient at the time of measurement of cardiovascular pressure (368) and transmit the cardiovascular pressure measurement and the measured posture to a network device (370). IMD 15 may include sensors 166 including accelerometers 167 for generating signals based on the orientation of the patient. Memory 170 may store data indicating one or more target postures, as well as possibly storing data indicating unacceptable postures. Processing circuitry 160 of IMD 15 may determine whether the posture of the patient matches the target posture(s).

The network device may determine if the posture is a target posture (372). The network device may further determine whether to store or discard the cardiovascular pressure measurement based on the determined posture (374). If processing circuitry 160 determines that the posture when the pressure measurement was made was the target posture, processing circuitry 160 may store the cardiovascular pressure measurement. However, if processing circuitry 160 of IMD 15 determines that the posture was not the target posture, processing circuitry 160 may discard the cardiovascular pressure measurement and possibly request another measurement from implantable pressure sensing device 12 after a given amount of time or upon determining that the patient's posture is the target posture. In some examples, IMD 15 may transmit the cardiovascular pressure measurement received from sensor 12 and the corresponding posture determined by IMD 15 to another device, e.g., any of the computing devices described herein, which may determine whether the corresponding posture is the target posture and determine whether to store or discard the pressure measurement based on the determination of whether the posture is the target posture.

The flowcharts of FIGS. 10-13 are intended to illustrate the functional operation of IMD 15, device 16, sensor device 12, external device 14, medical system 8, and other devices and systems described herein, and should not be construed as reflective of a specific form of software or hardware necessary to practice the methods described. Methods described in conjunction with flow diagrams presented herein may be implemented in a non-transitory computer-readable medium that includes instructions for causing a programmable processor to carry out the methods described. A non-transitory computer-readable medium includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented by processing circuitry hardware as execution of one or more software modules, which may be executed by themselves or in combination with other software.

The example methods illustrated by FIGS. 10-13 may be performed, by any one or more devices described herein, and may be performed, in part, by processing circuitry of any one or more devices described herein, such as by processing circuitry 160 of IMD 15, processing circuitry 200 of implantable pressure sensing device 12, which may correspond to sensor device 12 of FIGS. 1A-4B, computing devices 230A-230N, or any of the devices of FIG. 9.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

The following numbered examples demonstrate one or more aspects of the disclosure.

Example 1

A method for monitoring a cardiovascular pressure in a patient, the method including measuring, by pressure sensing circuitry of an implantable pressure sensing device, the cardiovascular pressure of the patient. The method further includes transmitting, via wireless communication circuitry of the implantable pressure sensing device, the measured cardiovascular pressure to another device. The method further includes determining, by processing circuitry of the other device, whether a posture of the patient at a time of the measured cardiovascular pressure was a target posture for cardiovascular pressure measurements. The method further includes determining, by the processing circuitry of the other device, whether to store or discard the transmitted cardiovascular pressure based on determining whether the posture was the target posture.

Example 2

The method of example 1, further including determining, by the processing circuitry of the other device, whether an activity level of the patient is below a threshold level. The method further includes determining, by the processing circuitry of the other device, whether to store or discard the transmitted cardiovascular pressure based on determining whether the activity level of the patient is below the threshold level.

Example 3

The method of any of examples 1-2 or combinations thereof, further including determining, by the processing circuitry of the other device, whether a heart rate of the patient is below a threshold rate. The method further includes determining, by the processing circuitry of the other device, whether to store or discard the transmitted cardiovascular pressure based on determining whether the heart rate of the patient is below the threshold rate.

Example 4

The method of any of examples 1-3 or combinations thereof, further including determining, by the processing circuitry of the other device, whether a respiration rate of the patient is below a threshold rate. The method further includes determining, by the processing circuitry of the other device, whether to store or discard the transmitted cardiovascular pressure based on determining whether the respiration rate of the patient is below the threshold rate.

Example 5

The method of any of examples 1-4 or combinations thereof, further including setting, by the processing circuitry of the other device, a timer based on determining that the posture was not the target posture. The method further includes, at an expiration of the timer, determining, by the processing circuitry of the other device, whether a posture of the patient is the target posture. The method further includes sending a trigger signal, via wireless communication circuitry of the other device, to the implantable pressure sensing device, wherein the implantable pressure sensing device measures the cardiovascular pressure of the patient using the pressure sensing circuitry in response to the trigger signal.

Example 6

The method of any of examples 1-5 or combinations thereof, further including transmitting, by wireless communication circuitry of the other device, the measured cardiovascular pressure to a third device. The method further includes transmitting, by the wireless communication circuitry of the other device, the time of day to the third device. The method further includes transmitting, by the wireless communication circuitry of the other device, the posture of the patient at the time of day to the third device.

Example 7

The method of any of examples 1-6 or combinations thereof, wherein the predetermined window includes of times of day after sunset local time and before sunrise local time.

Example 8

The method of any of examples 1-7 or combinations thereof, wherein determining whether the posture was the target posture includes measuring an accelerometer signal. The target posture includes a supine posture, a right-side-down posture when the implantable pressure sensing device is implanted in the left pulmonary artery, or a left-side-down posture when the implantable pressure sensing device is implanted in the right pulmonary artery.

Example 9

A medical device system for monitoring a cardiovascular pressure in a patient, the medical device system including an implantable pressure sensing device including wireless communication circuitry and pressure sensing circuitry configured to measure the cardiovascular pressure of the patient. The implantable pressure sensing device further includes processing circuitry configured to control the pressure sensing circuitry to measure the cardiovascular pressure of the patient. The processing circuitry of the implantable pressure sensing device is further configured to transmit the measured cardiovascular pressure to another device via the wireless communication circuitry. The medical device system further includes the other device including processing circuitry configured to determine whether a posture of the patient at a time of the measured cardiovascular pressure was a target posture for cardiovascular pressure measurements. The processing circuitry of the other device is further configured to determine whether to store or discard the transmitted cardiovascular pressure based on determining whether the posture was the target posture.

Example 10

The medical device system of example 9, wherein the other device further includes a housing containing the processing circuitry, wherein the housing is configured for implantation in the patient.

Example 11

The medical device system of any of examples 9-10 or combinations thereof, wherein the other device further includes a memory configured to store an upper bound for the predetermined window and a lower bound for the predetermined window and the posture of the patient at the time of day.

Example 12

The medical device system of any of examples 9-11 or combinations thereof, wherein the implantable pressure sensing device is configured for implantation in a vascular system of the patient, and the other device is configured for subcutaneous implantation in the patient.

Example 13

The medical device system of any of examples 9-12 or combinations thereof, wherein the processing circuitry of the other device is further configured to determine whether an activity level of the patient is below a threshold level, and determine whether to store or discard the transmitted cardiovascular pressure based on determining whether the activity level of the patient is below the threshold level.

Example 14

The medical device system of any of examples 9-13 or combinations thereof, wherein the processing circuitry of the other device is further configured to determine whether a heart rate of the patient is below a threshold rate, and determine whether to store or discard the transmitted cardiovascular pressure based on determining whether the heart rate of the patient is below the threshold rate.

Example 15

The medical device system of any of examples 9-14 or combinations thereof, wherein the processing circuitry of the other device is further configured to determine whether a respiration rate of the patient is below a threshold rate, and determine whether to store or discard the transmitted cardiovascular pressure based on determining whether the respiration rate of the patient is below the threshold rate.

Example 16

The medical device system of any of examples 9-15 or combinations thereof, wherein the processing circuitry of the other device is further configured to set a timer based on determining that the posture was not the target posture, and at an expiration of the timer, determine whether a posture of the patient is the target posture. The other device further includes wireless communication circuitry configured to send a trigger signal to the implantable pressure sensing device to cause the pressure sensing circuitry of the implantable pressure sensing device to measure the cardiovascular pressure of the patient in response to the trigger signal.

Example 17

The medical device system of any of examples 9-16 or combinations thereof, wherein the processing circuitry of the implantable pressure sensing device is further configured to determine that a time of day is within a predetermined window for cardiovascular pressure measurements, wherein the processing circuitry of the implantable pressure sensing device is configured to control the pressure sensing circuitry to measure the cardiovascular pressure in response to determining that the time of day is within the predetermined window, and wherein the other device further includes wireless communication circuitry configured to transmit the measured cardiovascular pressure to a third device, transmit the time of day to the third device, and transmit the posture of the patient at the time of day to the third device.

Example 18

The medical device system of any of examples 9-17 or combinations thereof, wherein the other device is configured for implantation in the patient, and wherein the other device further comprises sensing circuitry configured to generate a signal indicating the posture of the patient.

Example 19

The medical device system of any of examples 9-18, wherein the other device is configured to receive a signal indicating the posture of the patient from an implantable monitoring device.

Example 20

A method for monitoring a cardiovascular pressure in a patient, the method including determining, by processing circuitry of an implantable monitoring device, that a time of day is within a predetermined window for cardiovascular pressure measurements. The method further includes sensing, with sensing circuitry of the implantable monitoring device, posture of the patient during the predetermined window in response to the determination. The method further includes determining, by the processing circuitry of the implantable monitoring device, that the sensed posture of the patient is a target posture for cardiovascular pressure measurements. The method further includes sending a trigger signal, via wireless communication circuitry of the implantable monitoring device, to an implantable pressure sensing device, wherein the implantable pressure sensing device measures the cardiovascular pressure of the patient using pressure sensing circuitry in response to the trigger signal. The method further includes receiving, by the processing circuitry of the implantable monitoring device, the measured cardiovascular pressure of the patient from the implantable pressure sensing device via the wireless communication circuitry of the implantable monitoring device.

Example 21

The method of example 20, further including determining, by the processing circuitry of the implantable monitoring device, that the sensed posture of the patient is not the target posture. The method further includes refraining from sending the trigger signal via the wireless communication circuitry of the implantable monitoring device based on determining the sensed posture is not the target posture. The method further includes setting, by the processing circuitry of the implantable monitoring device, a timer. The method further includes at an expiration of the timer, with posture sensing circuitry of the implantable monitoring device, sensing posture of the patient. The method further includes determining, by the processing circuitry of the implantable monitoring device, that the sensed posture of the patient is the target posture. The method further includes sending the trigger signal, via the wireless communication circuitry of the implantable monitoring device, to the implantable pressure sensing device, based on determining the sensed posture is the target posture.

Example 22

The method of any of examples 20-21 or combinations thereof, further including determining, by the processing circuitry of the implantable monitoring device, whether a heart rate of the patient is below a threshold rate. The method further includes sending the trigger signal, via wireless communication circuitry of the implantable monitoring device, to an implantable pressure sensing device based on determining whether the heart rate of the patient is below the threshold rate.

Example 23

A medical device system for monitoring a cardiovascular pressure in a patient, the medical device system comprising an implantable monitoring device comprising wireless communication circuitry, processing circuitry configured to determine that a time of day is within a predetermined window for cardiovascular pressure measurements, and sensing circuitry configured to sense a posture of the patient during the predetermined window in response to the determination. The processing circuitry is further configured to determine that the sensed posture of the patient is a target posture for cardiovascular pressure measurements. The wireless communication circuitry is configured to send a trigger signal to an implantable pressure sensing device. The medical device system further comprises the implantable pressure sensing device comprising wireless communication circuitry configured to receive the trigger signal and pressure sensing circuitry configured to measure the cardiovascular pressure of the patient in response to the trigger signal. The wireless communication circuitry of the implantable pressure sensing device is further configured to transmit the measured cardiovascular pressure of the patient to the implantable monitoring device.

Example 24

The medical device system of example 23, wherein the processing circuitry of the implantable monitoring device is further configured to determine that the sensed posture of the patient is not the target posture. The wireless communication circuitry of the implantable monitoring device is further configured to refrain from sending the trigger signal based on determining the sensed posture is not the target posture. The processing circuitry of the implantable monitoring device is further configured to set a timer. The posture sensing circuitry of the implantable monitoring device is further configured to sense posture of the patient at an expiration of the timer. The processing circuitry of the implantable monitoring device is further configured to determine that the sensed posture of the patient is the target posture. The wireless communication circuitry of the implantable monitoring device is further configured to send the trigger signal to the implantable pressure sensing device, based on determining the sensed posture is the target posture.

Example 25

The medical device system of any of examples 23-24 or combinations thereof, wherein the processing circuitry of the implantable monitoring device is further configured to determine whether a heart rate of the patient is below a threshold rate. The wireless communication circuitry of the implantable monitoring device is further configured to send the trigger signal to an implantable pressure sensing device based on determining whether the heart rate of the patient is below the threshold rate.

Example 26

A method for monitoring a cardiovascular pressure in a patient, the method comprising determining, by processing circuitry of an implantable pressure sensing device, that a time of day is within a predetermined window for cardiovascular pressure measurements. The method further includes measuring, by pressure sensing circuitry of the implantable pressure sensing device, the cardiovascular pressure of the patient in response to the determination. The method also includes transmitting, via wireless communication circuitry of the implantable pressure sensing device, the measured cardiovascular pressure to another device. The method includes determining, by processing circuitry of the other device, whether a posture of the patient at the time of day was a target posture for cardiovascular pressure measurements, wherein the target posture comprises a supine posture, a right-side-down posture when the implantable pressure sensing device is implanted in the left pulmonary artery, or a left-side-down posture when the implantable pressure sensing device is implanted in the right pulmonary artery. The method further includes determining, by the processing circuitry of the other device, whether to store or discard the transmitted cardiovascular pressure based on determining whether the posture was the target posture.

Example 27

The method of any of examples 1-8 or combinations thereof, further including determining, by processing circuitry of the implantable pressure sensing device, that a time of day is within a predetermined window for cardiovascular pressure measurements, wherein measuring the cardiovascular pressure of the patient is in response to determining that the time of day is within the predetermined window.

Various aspects of this disclosure have been described. These and other aspects are within the scope of the following claims.

What is claimed is:

1. A method for monitoring a cardiovascular pressure in a patient, the method comprising:
   measuring, by pressure sensing circuitry of a first device implanted in a pulmonary artery of the patient, a first set of cardiovascular pressures of the patient;
   transmitting, via wireless communication circuitry of the first device, the measured first set of cardiovascular pressures to a second device;
   determining, by the second device, a first set of postures of the patient;
   thereafter communicating, by the second device, the determined first set of postures and the measured first set of cardiovascular pressures to a third device;
   determining, by the third device whether, at a time of measurement of a given one of the measured first set of cardiovascular pressures, the patient's determined posture was any target posture of a set of multiple target postures, wherein the set of multiple target postures is defined by a location in the pulmonary artery in which the first device is implanted;
   determining, by the third device, whether to store or discard the given measured cardiovascular pressure based on whether the posture was any target posture of the set of multiple target postures;
   determining, by the third device, whether a threshold number of cardiovascular pressure measurements have been stored;
   in response to a determination that the threshold number of cardiovascular pressure measurements have not been stored and the determination that the patient is in any target posture of the set of multiple target postures, setting, by the third device, a timer for a first amount of time, the expiration of which defines a second defined time for measuring a second set of cardiovascular pressures; and
   in response to arrival of the second defined time:
      measuring, by the first device, the second set of cardiovascular pressures of the patient;
      determining, by the second device, a second set of postures of the patient; and
      determining, by the third device, whether, at a time of measurement of a given one of the measured second set of cardiovascular pressures, the patient's determined posture was any target posture of the set of multiple target postures.

2. A method according to claim 1 wherein the second device is also implanted in the patient.

3. A method according to claim 2 wherein the third device is located outside the patient's body.

4. A method according to claim 1 wherein the third device is located outside the patient's body.

5. A method according to claim 1 wherein determining the patient's postures comprises measuring an accelerometer signal.

6. A method according to claim 1 wherein the first device is implanted in the patient's left pulmonary artery and the set of multiple target postures comprises a rightside-down posture.

7. A method according to claim 1 wherein the first device is implanted in the patient's right pulmonary artery and the set of multiple target postures comprises a leftside-down posture.

8. A method for monitoring a cardiovascular pressure in a patient, the method comprising:
   determining, by a first device, whether a first defined time for a cardiovascular pressure measurement has arrived;
   in response to arrival of the first defined time, determining, by the first device, whether the patient is in any target posture of a set of multiple target postures, wherein the set of multiple target postures is defined by a location in a pulmonary artery of a patient's body in which a pressure sensing device is implanted;
   in response to a determination that the patient is in any target posture of the set of multiple target postures, triggering by the first device, a measurement of the patient's cardiovascular pressure using the pressure sensing device;
   transmitting via wireless communication circuitry of the pressure sensing device, the measured cardiovascular pressure to the first device;
   determining, by the first device, whether a threshold number of pressure measurements have been taken;
   in response to a determination that the threshold number of pressure measurements have not been taken and the determination that the patient is in any target posture of the set of multiple target postures, setting, by the first device, a timer for a first amount of time, the expiration of which defines a second defined time for cardiovascular pressure measurement; and
   in response to arrival of the second defined time, again determining, by the first device, whether the patient is in any target posture of the set of multiple target postures.

9. A method according to claim 8 wherein the first device, in response to a determination that the patient is not in any target posture of the set of multiple target postures, initiates a timer interval, the expiration of which defines a third defined time for cardiovascular pressure measurement and wherein in response to arrival of the third defined time, again determining, by the first device, whether the patient is in any target posture of the set of multiple target postures.

10. A method according to claim 8, further comprising:
   in response to arrival of the first defined time, determining, by the first device, whether the patient's activity level is below a threshold level; and wherein triggering by the measurement of the patient's cardiovascular pressure occurs only when the patient is in any target posture of the set of multiple target postures and the patient's activity is below the threshold level.

11. A method according to claim 8, further comprising:
   in response to arrival of the first defined time, determining, by the first device, whether the patient's heart rate is below a threshold rate; and wherein triggering by the measurement of the patient's cardiovascular pressure occurs only when the patient is in any target posture of the set of multiple target postures and the patient's heart rate is below the threshold rate.

12. A method according to claim 8 wherein determining whether the patient is in any target posture of the set of multiple target postures comprises measuring an accelerometer signal.

13. A method according to claim 8 wherein the implantable pressure sensing device is implanted in the patient's left pulmonary artery and the target set of multiple target postures comprises a rightside-down posture.

14. A method according to claim 8 wherein the implantable pressure sensing device is implanted in the patient's right pulmonary artery and the set of multiple target postures comprises a leftside-down posture.

15. The method according to claim 8, further comprising:
in response to a determination that the threshold number of pressure measurements have not been taken and a determination that the patient is not in any target posture of the set of multiple target postures, setting, by the first device, the timer for a second amount of time, wherein the second amount of time is shorter than the first amount of time, and wherein the expiration of the second amount of time defines a third defined time for cardiovascular pressure measurement; and
in response to arrival of the third defined time, again determining, by the first device, whether the patient is in any target posture of the set of multiple target postures.

16. A method for monitoring a cardiovascular pressure in a patient using a pressure sensing device implanted in a pulmonary artery of the patient, the method comprising:
determining whether a first defined time for a cardiovascular pressure measurement has arrived;
in response to arrival of the first defined time, determining, whether the patient is in any target posture of a set of multiple target postures, wherein the set of multiple target postures is defined by a location in the pulmonary artery in which the pressure sensing device is implanted;
in response to a determination that the patient is in any target posture of the set of multiple target postures, measuring the patient's cardiovascular pre s sure using the pressure sensing device;
transmitting, via wireless communication circuitry of the pressure sensing device, the measured cardiovascular pressure to a second device;
determining whether a threshold number of pressure measurements have been taken;
in response to a determination that the threshold number of pressure measurements have not been taken and the determination that the patient is in any target posture of the set of multiple target postures, setting a timer for a first amount of time, the expiration of which defines a second defined time for cardiovascular pressure measurement; and
in response to arrival of the second defined time, again determining whether the patient is in any target posture of the set of multiple target postures.

17. A method according to claim 16, further comprising:
in response to a determination that the patient is not in any target posture of the set of multiple target postures, initiating a time interval, the expiration of which defines a third defined time for cardiovascular pressure measurement and wherein in response to arrival of the third defined time, again determining whether the patient is in any target posture of the set of multiple target postures.

18. A method according to claim 16, further comprising:
in response to arrival of the first defined time, determining whether the patient's activity level is below a threshold level; and wherein the measurement of the patient's cardiovascular pressure occurs only when the patient is in any target posture of the set of multiple target postures and the patient's activity is below the threshold level.

19. A method according to claim 16, further comprising:
in response to arrival of the first defined time, determining whether the patient's heart rate is below a threshold rate; and wherein the measurement of the patient's cardiovascular pressure occurs only when the patient is in any target posture of the set of multiple target postures and the patient's heart rate is below the threshold rate.

20. A method according to claim 16 wherein the implantable pressure sensing device is implanted in the patient's left pulmonary artery and the set of multiple target postures comprises a right-side-down posture.

21. A method according to claim 16 wherein the implantable pressure sensing device is implanted in the patient's right pulmonary artery and the target set of multiple target postures comprises a leftside-down posture.

* * * * *